United States Patent
Shin et al.

(10) Patent No.: US 9,972,784 B2
(45) Date of Patent: *May 15, 2018

(54) COMPOUNDS AND ORGANIC ELECTRONIC DEVICE USING SAME

(75) Inventors: Changhwan Shin, Daejeon (KR); Kongkyeom Kim, Daejeon (KR); Hyok Joon Kwon, Daejeon (KR); Dong Hoon Lee, Daejeon (KR); Jinyoung Lee, Daejeon (KR); Boonjae Jang, Daejeon (KR); Jungi Jang, Daejeon (KR); Hyungjin Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 70 days.

This patent is subject to a terminal disclaimer.

(21) Appl. No.: 14/125,509

(22) PCT Filed: Jun. 12, 2012

(86) PCT No.: PCT/KR2012/004627
§ 371 (c)(1),
(2), (4) Date: Dec. 11, 2013

(87) PCT Pub. No.: WO2012/173369
PCT Pub. Date: Dec. 20, 2012

(65) Prior Publication Data
US 2014/0110694 A1    Apr. 24, 2014

(30) Foreign Application Priority Data

Jun. 13, 2011  (KR) .................. 10-2011-0056777

(51) Int. Cl.
| | | |
|---|---|---|
| *H01L 51/50* | (2006.01) | |
| *H01L 51/00* | (2006.01) | |
| *C09K 11/06* | (2006.01) | |
| *H05B 33/10* | (2006.01) | |
| *C07D 487/04* | (2006.01) | |
| *C09B 57/00* | (2006.01) | |
| *C07F 9/6561* | (2006.01) | |

(52) U.S. Cl.
CPC ........ *H01L 51/0052* (2013.01); *C07D 487/04* (2013.01); *C07F 9/6561* (2013.01); *C09B 57/00* (2013.01); *C09K 11/06* (2013.01); *H01L 51/0058* (2013.01); *H01L 51/0072* (2013.01); *H05B 33/10* (2013.01); *C09K 2211/1007* (2013.01); *C09K 2211/1011* (2013.01); *C09K 2211/1014* (2013.01); *C09K 2211/1044* (2013.01); *H01L 51/006* (2013.01); *H01L 51/0068* (2013.01); *H01L 51/0077* (2013.01); *H01L 51/0081* (2013.01); *H01L 51/5072* (2013.01); *Y02E 10/549* (2013.01); *Y10S 428/917* (2013.01)

(58) Field of Classification Search
CPC .. C07D 401/04; C07D 401/14; C07D 487/04; C07D 487/06; C07D 487/08; H01L 51/50; H01L 51/5016; H01L 51/5072; H01L 51/0058; H01L 51/0072; H01L 51/006; H01L 51/0068; H01L 51/0077; H01L 51/0081; H01L 51/0052; C09K 11/06; C09K 2211/1007; C09K 2211/1011; C09K 2211/1014; C09K 2211/1044; C07F 9/6561; C09B 57/00; H05B 33/10; Y02E 10/549; Y10S 428/917
USPC ..... 546/23, 48; 313/500–512; 428/690, 917, 428/691; 257/40, 88–104, 257/E51.001–E51.052; 427/58, 66; 252/301.16–301.35
See application file for complete search history.

(56) References Cited

U.S. PATENT DOCUMENTS

| | | |
|---|---|---|
| 2005/0123795 A1 | 6/2005 | Lussier et al. |
| 2006/0269784 A1 | 11/2006 | Leipold et al. |
| 2007/0131929 A1 | 6/2007 | Bae et al. |
| 2010/0039024 A1* | 2/2010 | Wendeborn .......... C07D 209/58 313/504 |
| 2011/0127513 A1* | 6/2011 | Lee et al. ................ 257/40 |
| 2011/0284799 A1 | 11/2011 | Stoessel et al. |
| 2012/0261651 A1* | 10/2012 | Noto et al. ................. 257/40 |

FOREIGN PATENT DOCUMENTS

| | | |
|---|---|---|
| CN | 101291935 A | 10/2008 |
| CN | 101415718 A | 4/2009 |
| JP | 2004-095221 | 3/2004 |
| JP | 2004095221 A | 3/2004 |
| JP | 2007-109988 | 4/2007 |
| JP | 2010-278376 | 12/2010 |
| JP | 2010278376 A | 12/2010 |

(Continued)

OTHER PUBLICATIONS

Office Action of the U.S. Patent Office in U.S. Appl. No. 14/125,539 dated May 19, 2016; pp. 1-12.*

(Continued)

*Primary Examiner* — Andrew K Bohaty
*Assistant Examiner* — Dylan C Kershner
(74) *Attorney, Agent, or Firm* — Dentons US LLP

(57) ABSTRACT

The present invention provides a new compound and an organic electronic diode using the same. The compound according to the present invention may be used as hole injection, hole transport, electron injection and transport, and light emitting materials in an organic light emitting diode and an organic electronic diode, and the organic electronic diode according to the present invention exhibits excellent efficiency, driving voltage, and life-span properties.

4 Claims, 2 Drawing Sheets

(56) References Cited

FOREIGN PATENT DOCUMENTS

| KR | 10-2005-0037337 | | 4/2005 |
|---|---|---|---|
| KR | 10-2005-0037337 | A | 4/2005 |
| KR | 20050037337 | A | 4/2005 |
| KR | 20060109524 | A | 10/2006 |
| KR | 10-2007-0095042 | | 9/2007 |
| KR | 10-2011-0042127 | A | 4/2011 |
| WO | 2006/080640 | A1 | 8/2006 |
| WO | 2007-064479 | | 6/2007 |
| WO | 2007-069847 | | 6/2007 |
| WO | 2007-095118 | | 8/2007 |
| WO | 2007095118 | A | 8/2007 |
| WO | 2008120957 | A1 | 10/2008 |
| WO | 2009-100991 | | 8/2009 |
| WO | 2010-062065 | | 6/2010 |
| WO | 2010/086089 | A1 | 8/2010 |
| WO | 2011/010842 | A2 | 1/2011 |
| WO | 2011-021385 | | 2/2011 |
| WO | 2011021385 | A1 | 2/2011 |
| WO | WO 2011021385 A1 * | | 2/2011 |

OTHER PUBLICATIONS

"Multifunctional Deep-Blue Emitter Comprising an Anthracene Cor and Terminal Triphenylphosphine Oxide Groups"; Chien et al; Adv. Funct. Mater. 2009, 19, 560-566.

Office Action of Chinese Patent Office in Appl'n No. 201280029198.5, dated Jun. 17, 2015.

\* cited by examiner

[Figure 1]
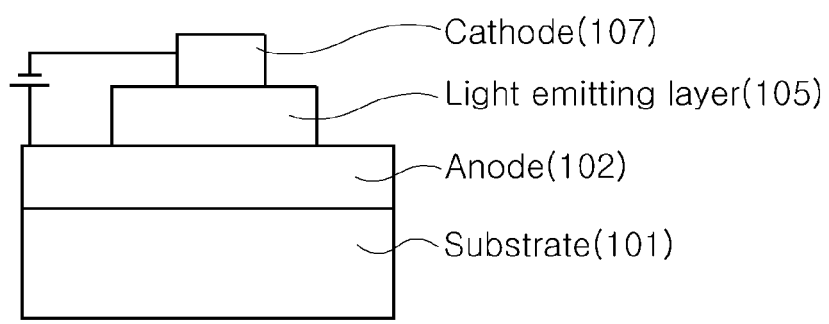
[Figure 2]
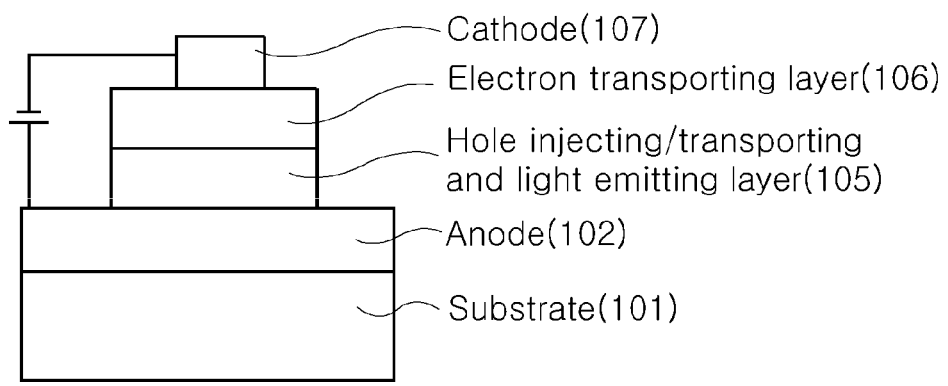

[Figure 3]
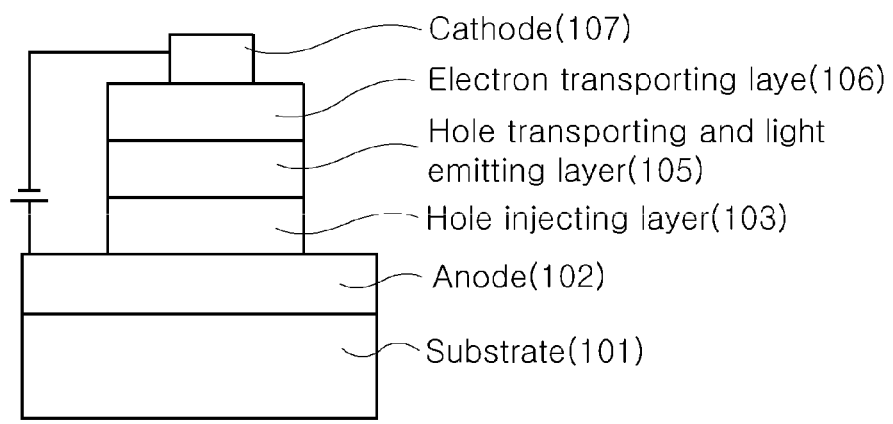
[Figure 4]
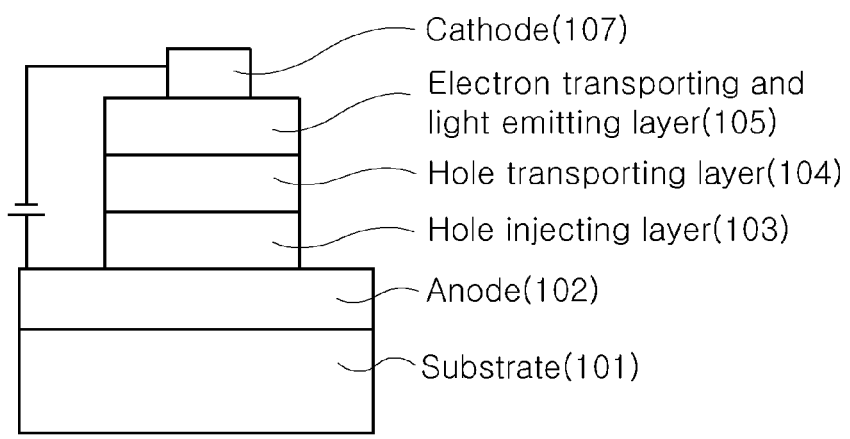

COMPOUNDS AND ORGANIC ELECTRONIC DEVICE USING SAME

TECHNICAL FIELD

This application is a 35 USC § 371 National Stage entry of International Application No. PCT/KR2012/004627, filed on Jun. 12, 2012, which claims priority of Korean Application No. 10-2011-0056777, filed on Jun. 13, 2011, all of which are hereby incorporated by reference in their entirety.

The present invention relates to a new compound and an organic electronic diode using the same.

BACKGROUND ART

In the present specification, an organic electronic diode is an electronic diode using an organic semiconductor material, and requires exchange of holes and/or electrons between an electrode and the organic semiconductor material. The organic electronic diode may be largely divided into the following two categories according to an operation principle. First, there is an electronic diode in which an exciton is formed in an organic layer by a photon that flows from an external light source to the diode, the exciton is separated into electrons and holes, and the electrons and the holes are transferred to the different electrodes and used as a current source (voltage source). Second, there is an electronic diode in which holes and/or electrons are injected into an organic semiconductor material layer forming an interface to the electrode by applying a voltage or a current to two or more electrodes to operate the diode by the injected electrons and holes.

Examples of the organic electronic diode comprise an organic light emitting diode, an organic solar cell, an organic photoconductor (OPC) drum, an organic transistor and the like, and all of the organic electronic diodes require electron/hole injection materials, electron/hole extraction materials, electron/hole transport materials or a light emitting material in order to drive the diode. Hereinafter, an organic light emitting diode will be mainly described in detail, but in the organic electronic diodes, all of the electron/hole injection materials, the electron/hole extraction materials, the electron/hole transport materials or the light emitting material are operated on the basis of the similar principle.

In general, an organic light emitting phenomenon means a phenomenon that converts electric energy into light energy by using an organic material. The organic light emitting diode using the organic light emitting phenomenon has a structure generally comprising an anode, a cathode, and an organic layer between the anode and the cathode. Herein, most organic layers have a multilayered structure constituted by different materials in order to increase efficiency and stability of the organic light emitting diode, and for example, may comprise a hole injection layer, a hole transport layer, a light emitting layer, an electron transport layer, an electron injection layer and the like. In the structure of the organic light emitting diode, if a voltage is applied between two electrodes, holes are injected from an anode and electrons are injected from a cathode to the organic layer, and when the injected holes and the electrons meet each other, an exciton is formed, and light is emitted when the exciton falls to a bottom state. It is known that this organic light emitting diode has properties such as magnetic light emission, high brightness, high efficiency, low driving voltage, a wide viewing angle, high contrast and high response speed.

In the organic light emitting diode, the material used in the organic layer may be classified into a light emitting material and a charge transport material, for example, a hole injection material, a hole transport material, an electron transport material, an electron injection material and the like according to a function thereof. The light emitting material is classified into blue, green, and red light emitting materials and yellow and orange light emitting materials required to realize better natural colors according to the light emitting color. Further, a host/dopant system may be used as the light emitting material in order to increase color purity and increase light emitting efficiency through transferring of energy. The principle is that if a small amount of dopant that has a smaller energy band gap than a host mainly forming the light emitting layer and excellent light emitting efficiency is mixed with the light emitting layer, the exciton generated in the host is transported to the dopant to emit light at high efficiency. In this case, since the wavelength of the host moves to the wavelength bandwidth of the dopant, a desired wavelength of light may be obtained according to the kind of used dopant.

In order to sufficiently show excellent properties of the aforementioned organic light emitting diode, a material constituting the organic layer in the diode, for example, the hole injection material, the hole transport material, the light emitting material, the electron transport material, the electron injection material and the like should be supported by stable and efficient materials in advance, but development of a stable and efficient organic layer material for organic light emitting diodes has not yet been sufficiently made, such that there is a demand for developing a new material.

DISCLOSURE

Technical Problem

The present inventors found out a compound having a new structure. Further, the present inventors found out the fact that in the case where an organic layer of an organic electronic diode is formed by using the new compound, effects of an increase in efficiency of the diode, a reduction in driving voltage, and an increase in stability can be exhibited.

Accordingly, the present invention has been made in an effort to provide a new compound and an organic electronic diode using the same.

Technical Solution

An exemplary embodiment of the present invention provides a compound represented by the following Formula 1:

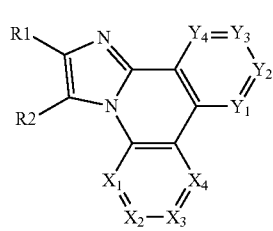

[Formula 1]

In Formula 1,
$X_1$ is N or CR3, $X_2$ is N or CR4, $X_3$ is N or CR5, $X_4$ is N or CR6, $Y_1$ is N or CR7, $Y_2$ is N or CR8, $Y_3$ is N or CR9, $Y_4$ is N or CR10, $X_1$ to $X_4$ and $Y_1$ to $Y_4$ are not all N, R3 to R10 are each independently -(L)p-(Y)q or a group represented by Formula 1A, at least one of R3 to R10 is the group represented by Formula 1A, p is an integer of 0 to 10, q is an integer of 1 to 10, and two or more adjacent groups of R3 to R10 may form a monocycle or polycycle,

[Formula 1A]

L is oxygen; sulfur; substituted or unsubstituted nitrogen; substituted or unsubstituted phosphorus; a substituted or unsubstituted arylene group; a substituted or unsubstituted alkenylene group; a substituted or unsubstituted fluorenylene group; a substituted or unsubstituted carbazolylene group; or a substituted or unsubstituted heteroarylene group comprising one or more of N, O and S atoms, Y is hydrogen; heavy hydrogen; a halogen group; a nitrile group; a nitro group; a hydroxy group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group comprising one or more of N, O and S atoms, R1 and R2 may be connected to each other to form or not to form a substituted or unsubstituted aliphatic, aromatic or heteroaromatic monocycle or polycycle, and in the case where R1 and R2 does not form the cycle, R1 and R2 are the same as or different from each other and each independently hydrogen, a substituted or unsubstituted $C_3$~$C_{40}$ cycloalkyl group; a substituted or unsubstituted $C_6$~$C_{60}$ aryl group; a substituted or unsubstituted $C_2$~$C_{40}$ alkenyl group; or a substituted or unsubstituted $C_2$~$C_{60}$ heterocyclic group, the aromatic or heteroaromatic monocycle and polycycle formed by connecting R1, R2, and R1 and R2 to each other may be each independently substituted by -(L)p-(Y)q, in the case where two or more L and two or more Y are present, L and Y are each independently the same as or different from each other, A are each independently O, S or Se, $Ar_1$ and $Ar_2$ are each independently a substituted or unsubstituted aryl group; or a substituted or unsubstituted heterocyclic group comprising one or more of N, O and S atoms, $Ar_3$ are each independently a substituted or unsubstituted arylene group; or a substituted or unsubstituted heteroarylene group comprising one or more of N, O and S atoms.

Another exemplary embodiment of the present invention provides an organic electronic diode which comprises a first electrode, a second electrode, and one or more organic layers interposed between the first electrode and the second electrode, wherein one or more layers of the organic layers comprise a compound represented by Formula 1.

Advantageous Effects

The new compound according to the present invention may be used as a material of an organic layer of an organic light emitting diode and an organic electronic diode by introducing various aryl groups, heteroaryl groups, arylamine groups and the like. The organic light emitting diode and the organic electronic diode using a compound represented by Formula 1 according to the present invention as the material of the organic layer exhibit excellent efficiency, driving voltage, and life-span properties.

BRIEF DESCRIPTION OF THE DRAWINGS

FIG. 1 illustrates an example of an organic light emitting diode having a structure where an anode 102, a light emitting layer 105 and a cathode 107 are sequentially laminated on a substrate 101.

FIG. 2 illustrates an example of an organic light emitting diode having a structure where an anode 102, hole injection/hole transport and light emitting layers 105, an electron transport layer 106 and a cathode 107 are sequentially laminated on a substrate 101.

FIG. 3 illustrates an example of an organic light emitting diode having a structure where a substrate 101, an anode 102, a hole injection layer 103, hole transport and light emitting layers 105, an electron transport layer 106 and a cathode 107 are sequentially laminated.

FIG. 4 illustrates an example of an organic light emitting diode having a structure where a substrate 101, an anode 102, a hole injection layer 103, a hole transport layer 104, electron transport and light emitting layers 105, and a cathode 107 are sequentially laminated.

BEST MODE

Hereinafter, the present invention will be described in more detail.

A new compound according to the present invention is represented by Formula 1.

In Formula 1, in the case where R1 and R2 are connected to each other to form one cycle, the compound may be represented by the following Formula 2.

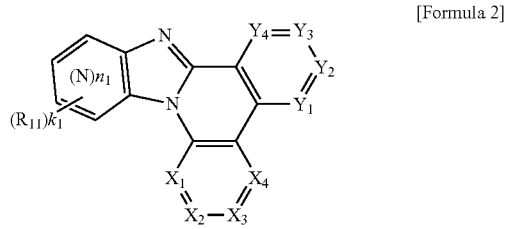

[Formula 2]

In Formula 2, $X_1$ to $X_4$, and $Y_1$ to $Y_4$ are as defined in Formula 1,

N of $(N)n_1$ means a nitrogen atom and also that the nitrogen atom may replace a carbon atom in a benzene cycle, $n_1$ of $(N)n_1$ is an integer of 0 to 6, $R_{11}$ is the same as definition of R3 to R10 of Formula 1, and $k_1$ is an integer of 0 to 4.

In Formula 1, in the case where R1 and R2 are connected to each other to form a polycycle of two or more cycles, the compound may be represented by the following Formula 3 or 4.

[Formula 3]

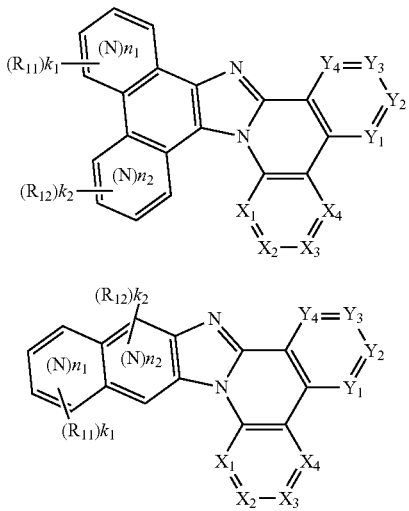

[Formula 4]

In Formula 3 and 4, $X_1$ to $X_4$, and $Y_1$ to $Y_4$ are as defined in Formula 1, N of $(N)n_1$ and $(N)n_2$ means a nitrogen atom and also that the nitrogen atom may replace a carbon atom in a benzene cycle, $n_1$ of $(N)n_1$ is an integer of 0 to 2, $n_2$ of $(N)n_2$ is an integer of 0 to 2, $R_{11}$ and $R_{12}$ are each independently the same as definition of R3 to R10 of Formula 1, and $k_1$ is an integer of 0 to 4, and $k_2$ is an integer of 0 to 4.

In Formula 1, in the case where R1 and R2 do not form a cycle, R1 and R2 may be a phenyl group substituted or unsubstituted by $R_{11}$ and $R_{12}$ or a hexagonal heteroaromatic cycle group that is substituted or unsubstituted by $R_{11}$ and $R_{12}$ and comprises a nitrogen (N) atom. For example, Formula 1 may be represented by the following Formula 5.

[Formula 5]

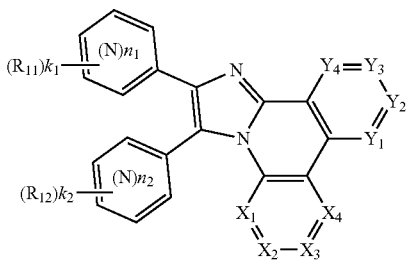

In Formula 5, $X_1$ to $X_4$, and $Y_1$ to $Y_4$ are as defined in Formula 1,

N of $(N)n_1$ and $(N)n_2$ means a nitrogen atom and also that the nitrogen atom may replace a carbon atom in a benzene cycle, $n_1$ of $(N)n_1$ is an integer of 0 to 2, $n_2$ of $(N)n_2$ is an integer of 0 to 2, $R_{11}$ and $R_{12}$ are each independently the same as definition of R3 to R10 of Formula 1, and $k_1$ is an integer of 0 to 4, and $k_2$ is an integer of 0 to 4.

In the compound according to the present invention, substituent groups of Formula 1 will be described in more detail below.

The alkyl group may be a straight or branched chain, and the number of carbon atoms is not particularly limited but is preferably 1 to 12. Specific examples thereof comprise a methyl group, an ethyl group, a propyl group, an isopropyl group, a butyl group, a t-butyl group, a pentyl group, a hexyl group, a heptyl group and the like, but are not limited thereto.

The alkenyl group may be a straight or branched chain, and the number of carbon atoms is not particularly limited but is preferably 2 to 12. Specific examples thereof comprise an alkenyl group connected to an aryl group such as a stylbenyl group and a styrenyl group, but are not limited thereto.

The alkynyl group may be a straight or branched chain, and the number of carbon atoms is not particularly limited but is preferably 2 to 12. Specific examples thereof comprise an ethinyl group, a propynyl group and the like, but are not limited thereto.

It is preferable that the cycloalkyl group has the 3 to 12 carbon atoms and do not provide steric hindrance. Specific examples thereof comprise a cyclopentyl group, a cyclohexyl group and the like, but are not limited thereto.

It is preferable that the cycloalkenyl group has 3 to 12 carbon atoms, and more specific examples thereof may comprise a cycle compound having ethenylene in a pentagonal or hexagonal cycle thereof, but are not limited thereto.

It is preferable that the alkoxy group has 1 to 12 carbon atoms, and more specific examples thereof may comprise methoxy, ethoxy, isopropyloxy and the like, but are not limited thereto.

It is preferable that the aryloxy group have 6 to 20 carbon atoms, and more specific examples thereof may comprise phenyloxy, cyclohexyloxy, naphthyloxy, diphenyloxy and the like, but are not limited thereto.

It is preferable that the alkylamine group have 1 to 30 carbon atoms, and more specific examples thereof may comprise a methylamine group, a dimethylamine group, an ethylamine group, a diethylamine group and the like, but are not limited thereto.

It is preferable that the arylamine group have 5 to 30 carbon atoms, and more specific examples thereof comprise a phenylamine group, a naphthylamine group, a biphenylamine group, an anthracenylamine group, a 3-methylphenylamine group, a 4-methyl-naphthylamine group, a 2-methyl-biphenylamine group, a 9-methyl-anthracenylamine group, a diphenylamine group, a phenylnaphthyl amine group, a ditolylamine group, a phenyltolylamine group, a triphenylamine group and the like, but are not limited thereto.

The aryl group may be a monocycle or polycycle, and the number of carbon atoms is not particularly limited but is preferably 6 to 40. Examples of the monocyclic aryl group may comprise a phenyl group, a biphenyl group, a terphenyl group, stilben and the like, and examples of the polycyclic aryl group may comprise a naphthyl group, an anthracenyl group, a phenanthrene group, a pyrenyl group, a perylenyl group, a cryxenyl group and the like, but are not limited thereto.

The heteroaryl group is a heteroatom, a cyclic group comprising O, N, S or P, and the number of carbon atoms is not particularly limited, but is preferably 3 to 30. Examples of the heterocyclic group comprise a carbazole group, a thiophene group, a furan group, a pyrrole group, an imidazole group, a thiazole group, an oxazole group, an oxadiazole group, a triazole group, a pyridyl group, a pyradazine group, a quinolynyl group, an isoquinolynyl group, an acrydyl group and the like, and the compounds of the following Structural Formulas are preferable but are not limited thereto.

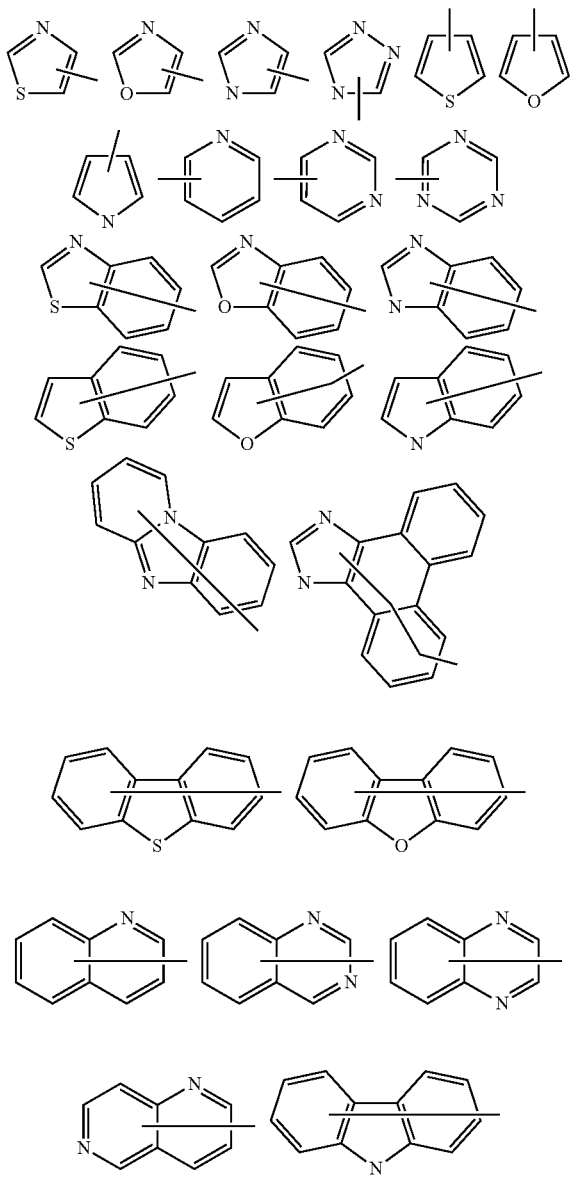

Examples of the halogen group may comprise fluorine, chlorine, bromine, iodine and the like, but are not limited thereto.

Specific examples of the arylene group may comprise a phenylene group, a biphenylene group, a naphthalenyl group, a binaphthalene group, an anthracenylene group, a fluorenylene group, a crycenylene group, a phenanthrenylene group and the like, but are not limited thereto.

Examples of the heterocycloalkyl group may comprise a cyclic group comprising a heteroatom such as N, S or O.

Further, in the present specification, the term "substituted or unsubstituted" means that substitution is performed by one or more substituent groups selected from the group consisting of heavy hydrogen, a halogen group, an alkyl group, an alkenyl group, an alkoxy group, a silyl group, an arylalkenyl group, an aryl group, a heteroaryl group, a carbazole group, an arylamine group, and a fluorenyl group substituted or unsubstituted by an aryl group, and a nitrile group, or there is no substituent group.

R1, R2, $X_1$ to $X_4$, $Y_1$ to $Y_4$, $Ar_1$ to $Ar_3$, and A of Formula 1 may be further substituted by an additional substituent group, and examples thereof may comprise a halogen group, an alkyl group, an alkenyl group, an alkoxy group, a silyl group, an arylalkenyl group, an aryl group, a heteroaryl group, a carbazole group, an arylamine group, a fluorenyl group substituted or unsubstituted by an aryl group, a nitrile group and the like, but are not limited thereto.

In the present invention, Formula 1 may be represented by the following Formula 6, but is not limited thereto.

[Formula 6]

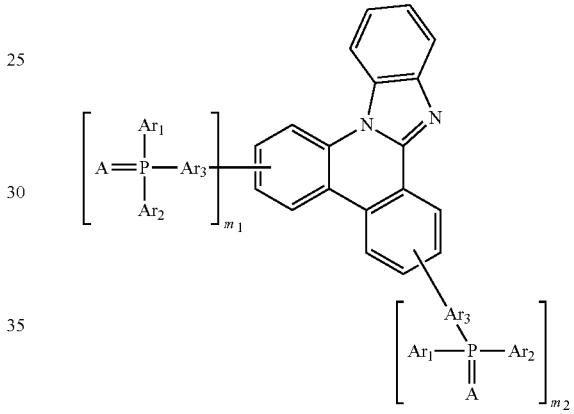

In Formula 6, $Ar_1$ to $Ar_3$, and A are as defined in Formula 1, and $m_1$ is an integer of 0 to 4, $m_2$ is an integer of 0 to 4, and $m_1$ and $m_2$ are not simultaneously 0.

$Ar_3$ of Formula 1 may be a substituted or unsubstituted arylene group selected from the group consisting of a phenylene group, a biphenylene group, a naphthalenyl group, a binaphthalene group, an anthracenylene group, a fluorenylene group, a crycenylene group, and a phenanthrenylene group.

Furthermore, $Ar_3$ of Formula 1 may be an arylene group selected from the group consisting of following formulae:

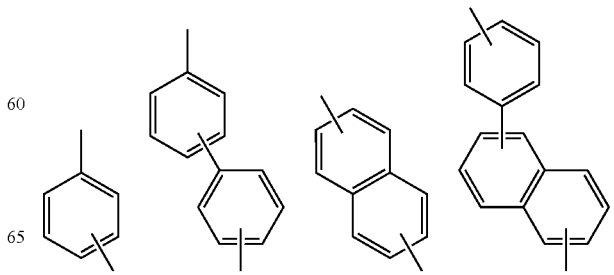

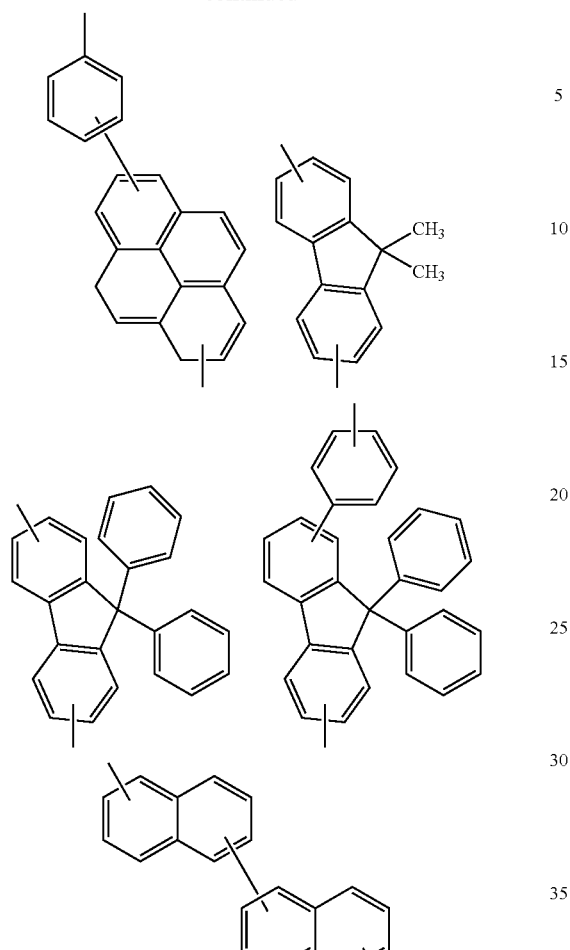
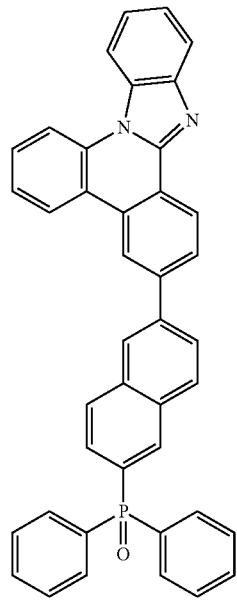
Preferable specific examples of the compound represented by Formula 1 comprise the following compounds, but are not limited thereto.
[Formula 1-1]
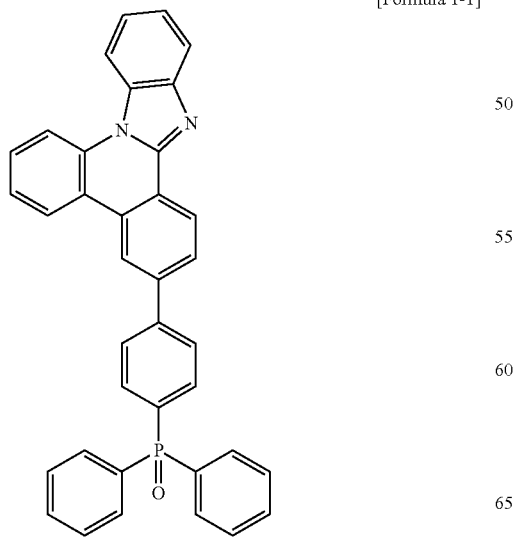
[Formula 1-2]
[Formula 1-3]
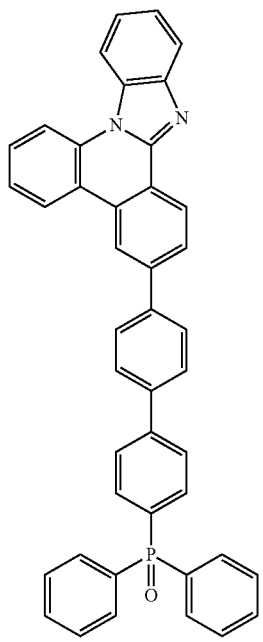

[Formula 1-4]
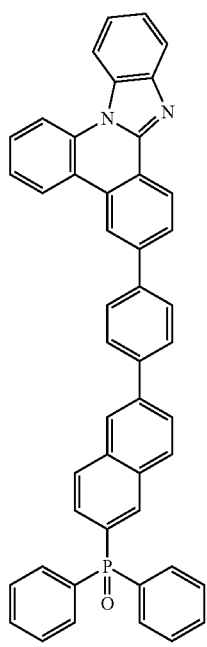
[Formula 1-6]
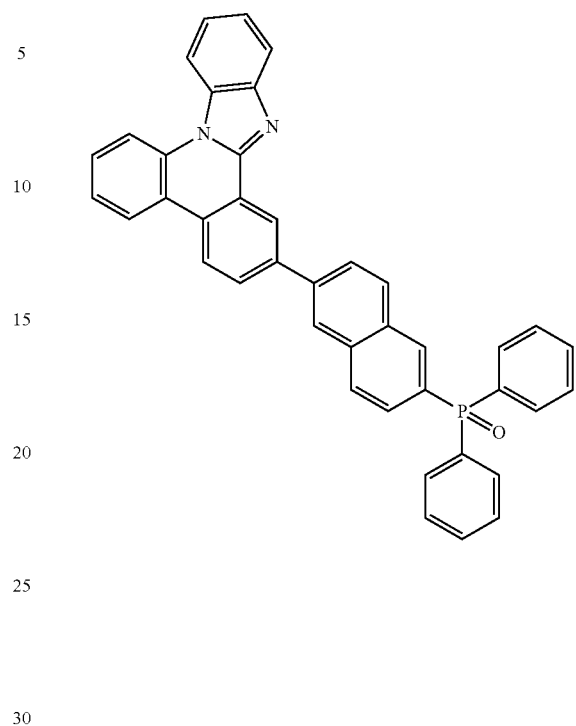
[Formula 1-5]
[Formula 1-7]
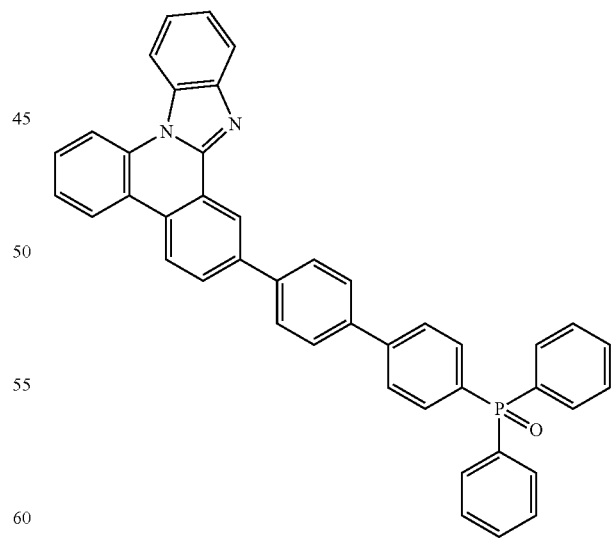

[Formula 1-8]
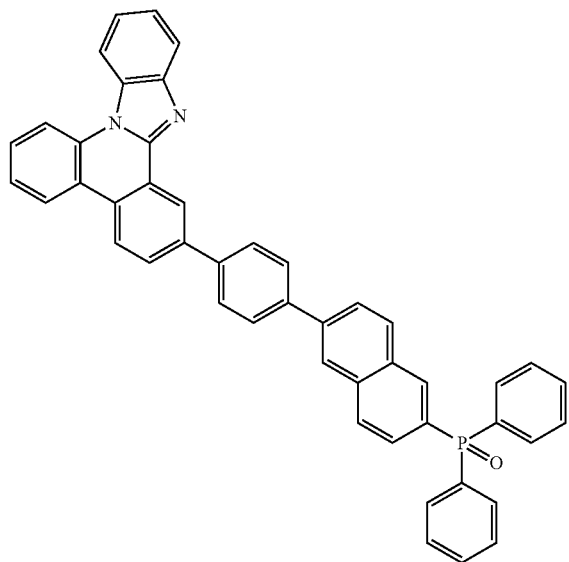
[Formula 1-9]
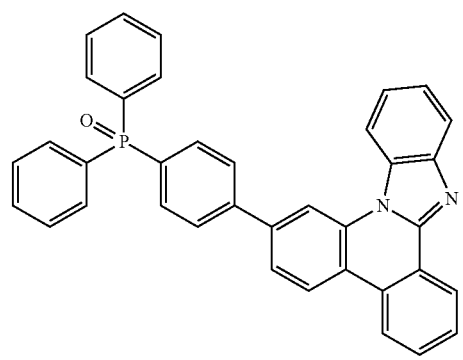
[Formula 1-10]
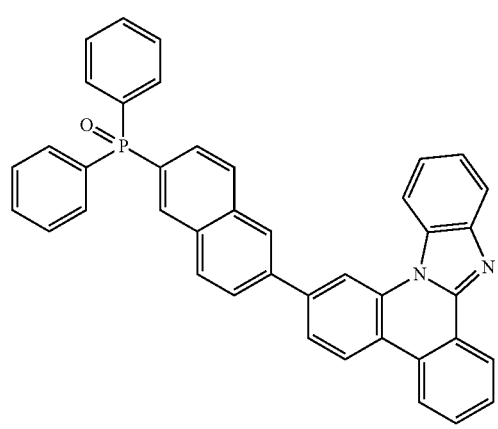
[Formula 1-11]
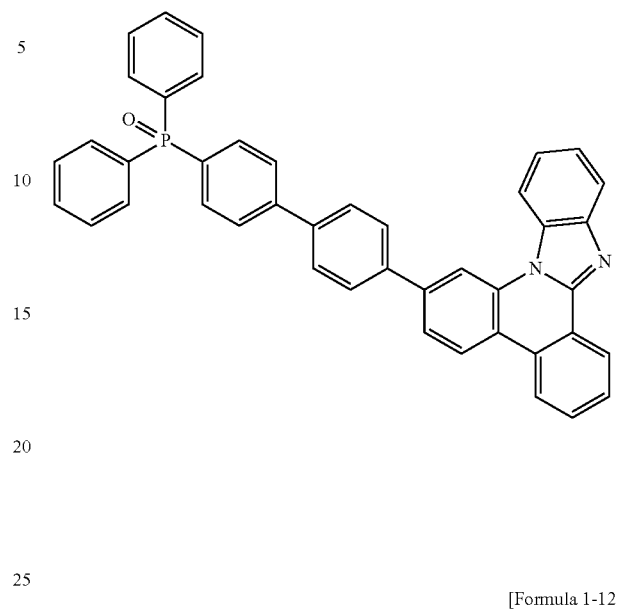
[Formula 1-12]
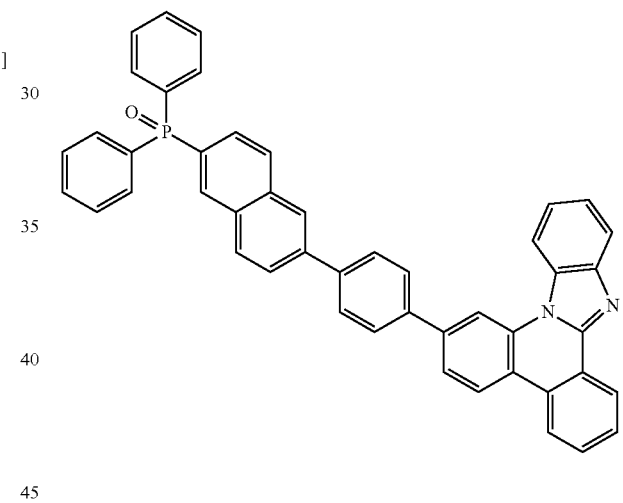
[Formula 1-13]
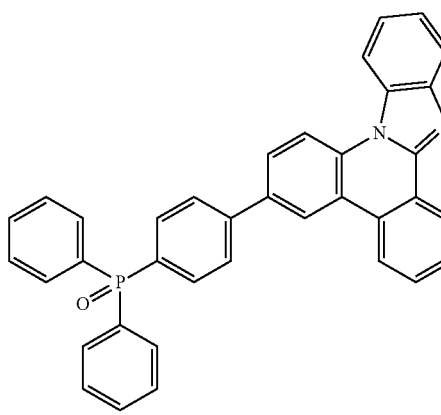

[Formula 1-14]
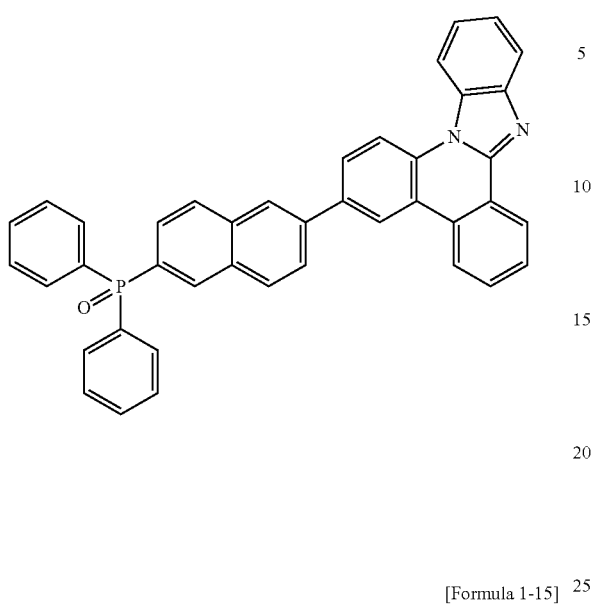
[Formula 1-15]
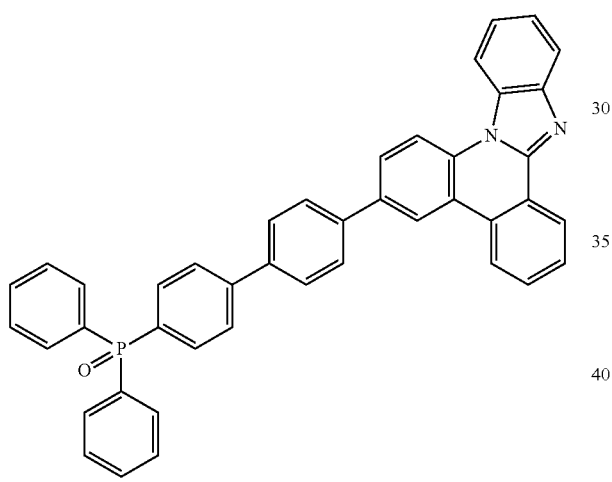
[Formula 1-16]
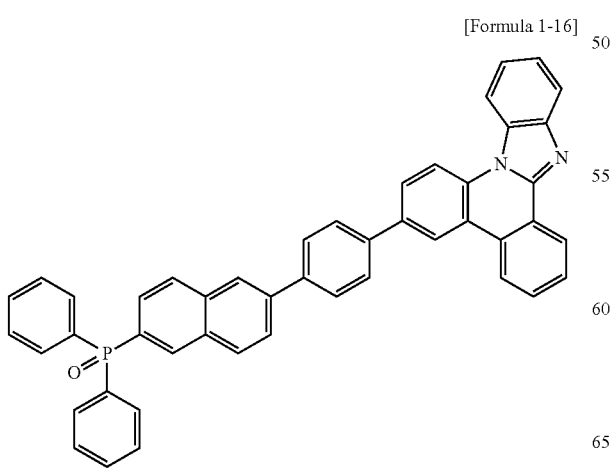
[Formula 1-17]
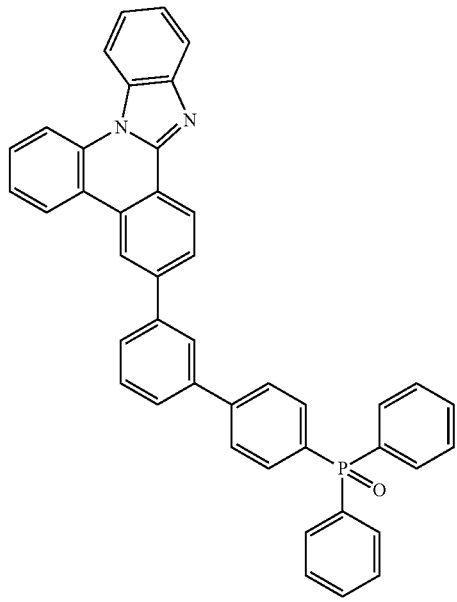
[Formula 1-18]
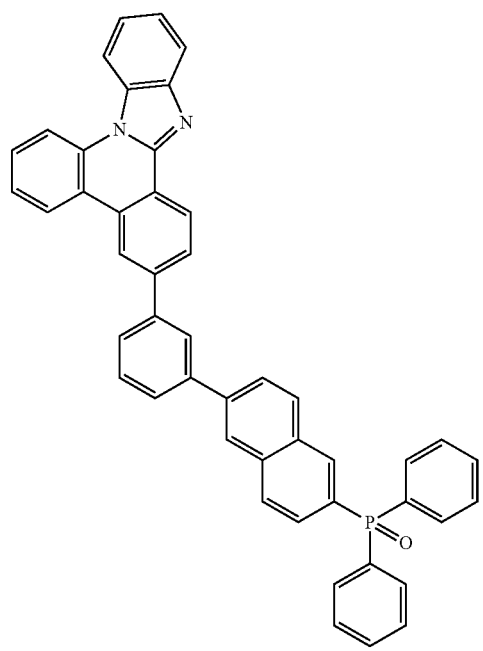

[Formula 1-19]
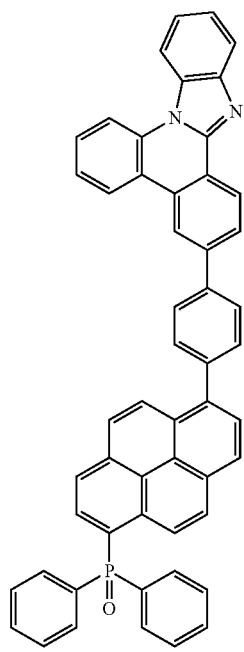
[Formula 1-20]
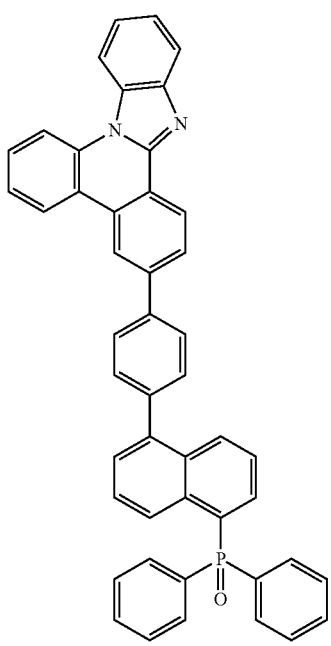
[Formula 1-21]
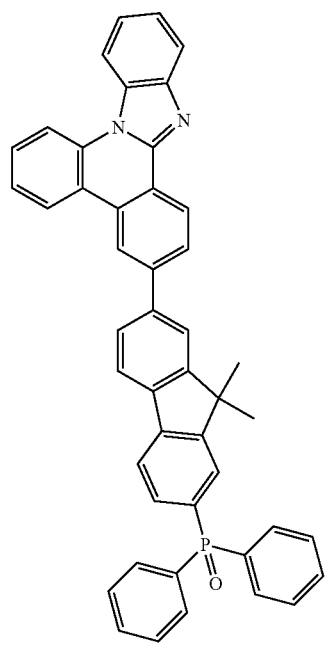
[Formula 1-22]
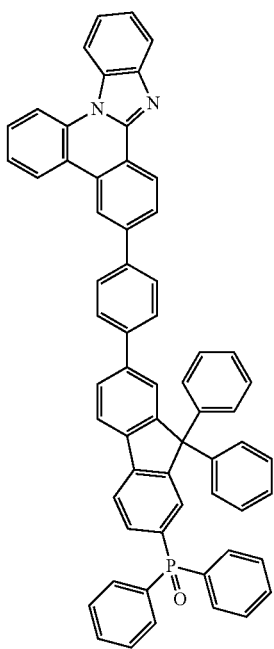

[Formula 1-23]
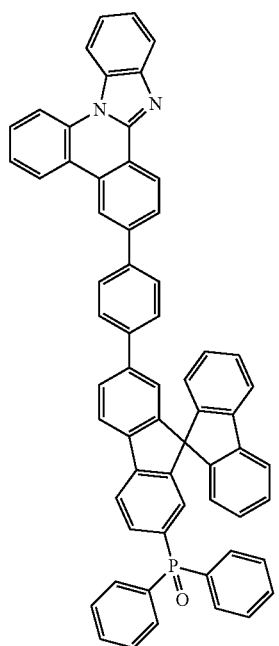
[Formula 1-25]
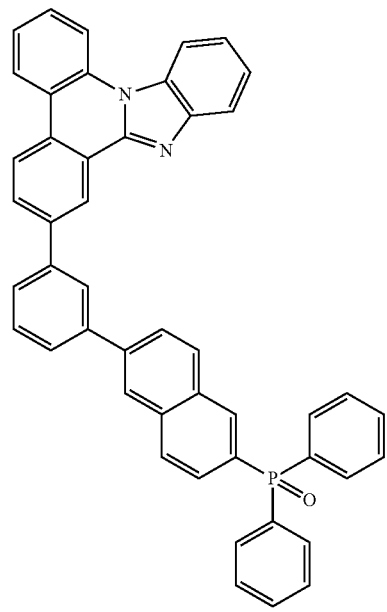
[Formula 1-24]
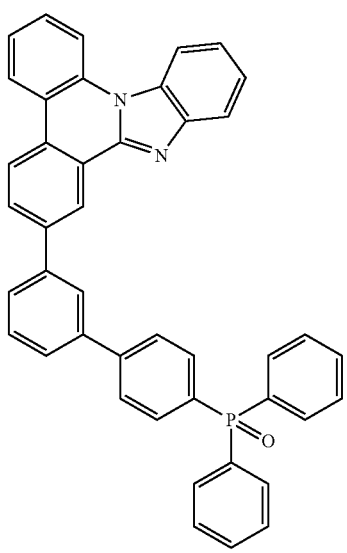
[Formula 1-26]
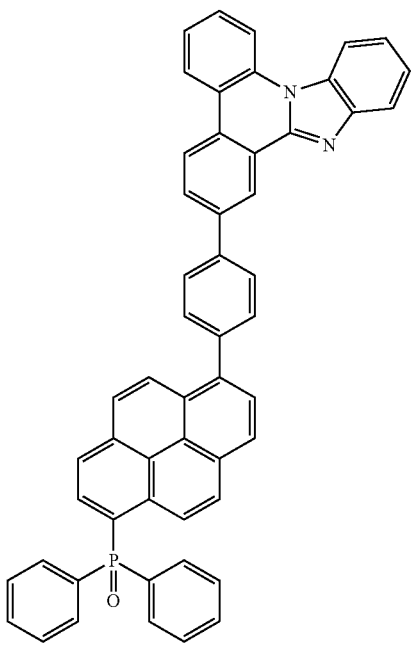

-continued
[Formula 1-27]
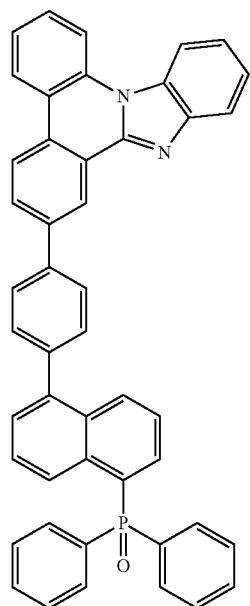
[Formula 1-28]
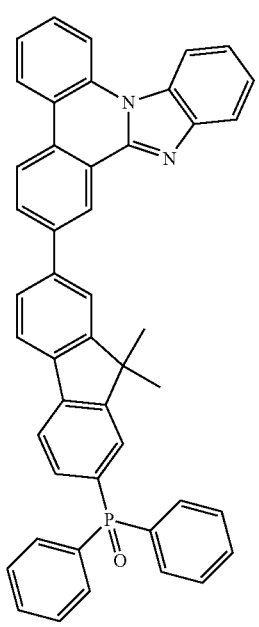
[Formula 1-29]
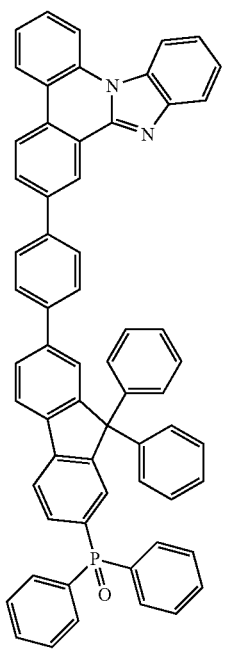
[Formula 1-30]
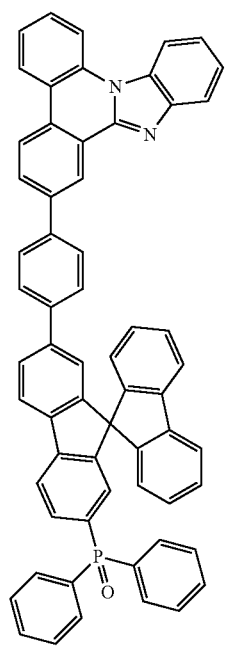

[Formula 1-31]
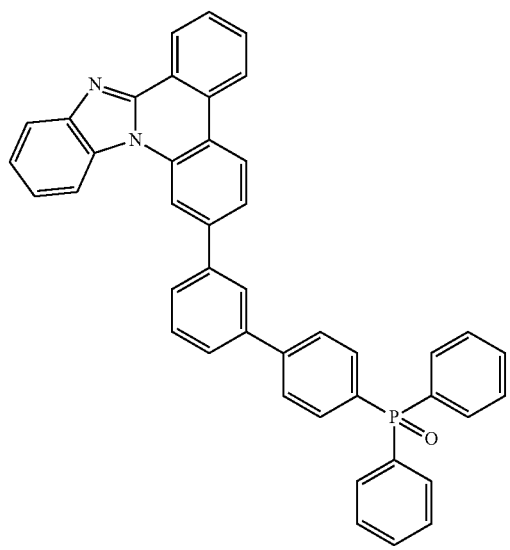
[Formula 1-33]
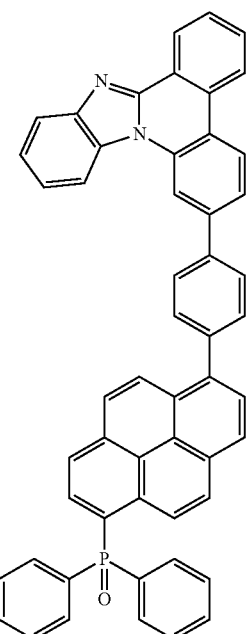
[Formula 1-32]
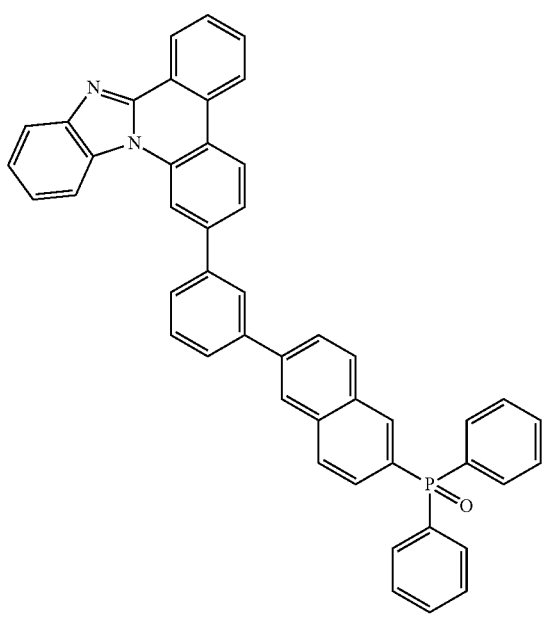
[Formula 1-34]
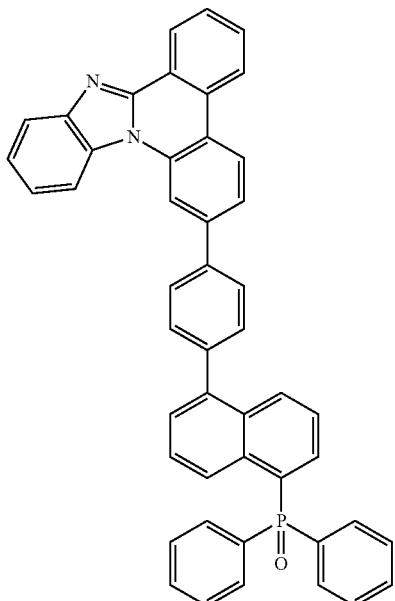

[Formula 1-35]
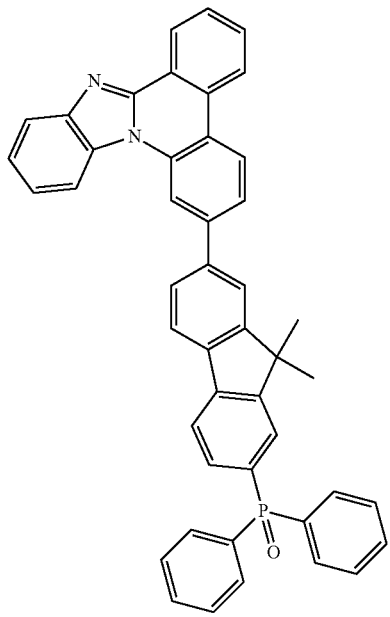
[Formula 1-36]
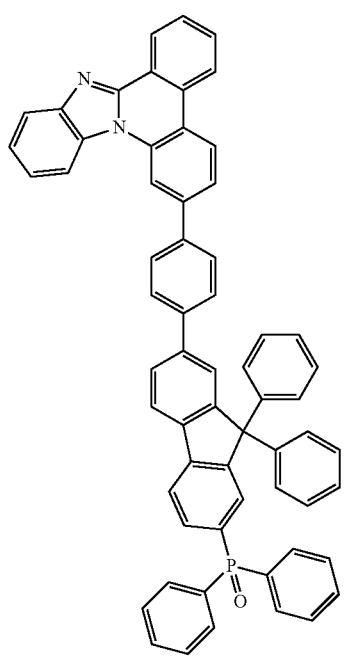
[Formula 1-37]
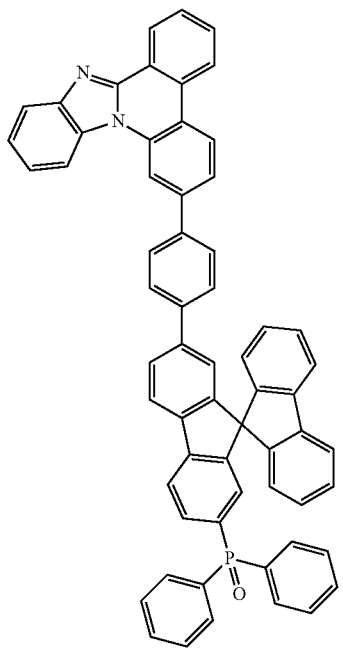
[Formula 1-38]
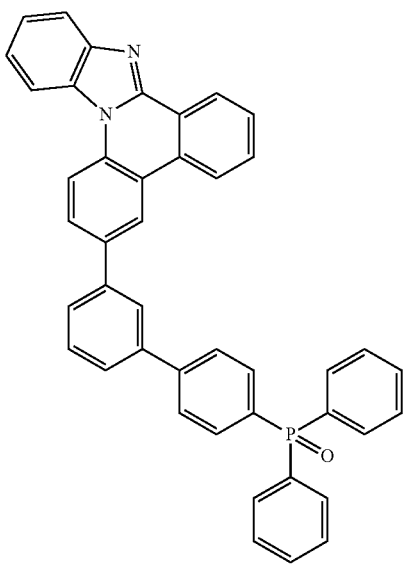

-continued
[Formula 1-39]
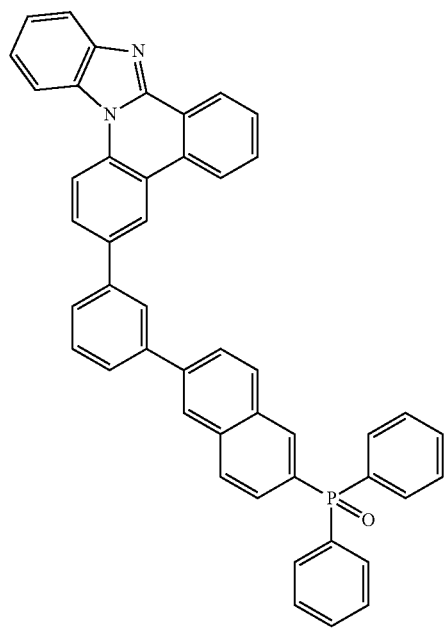
[Formula 1-40]
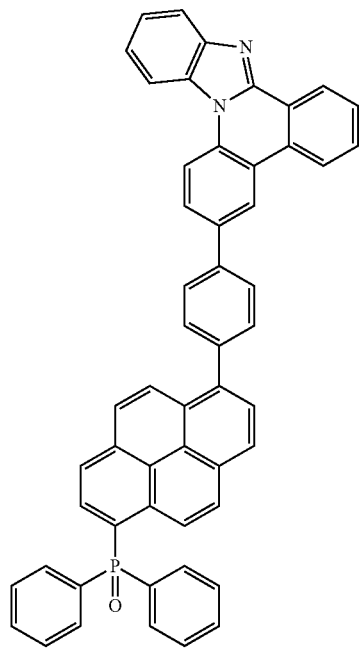
-continued
[Formula 1-41]
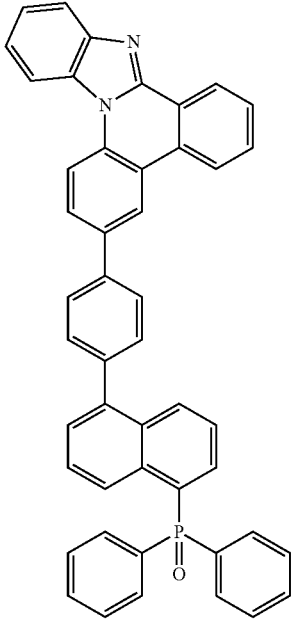
[Formula 1-42]
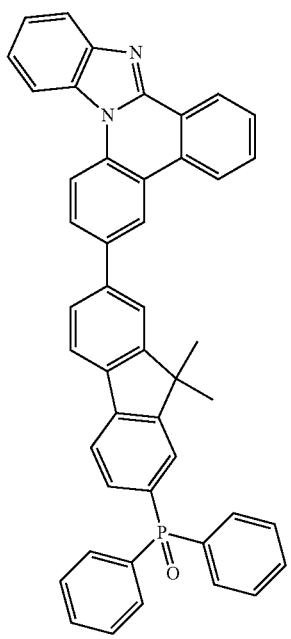

[Formula 1-43]
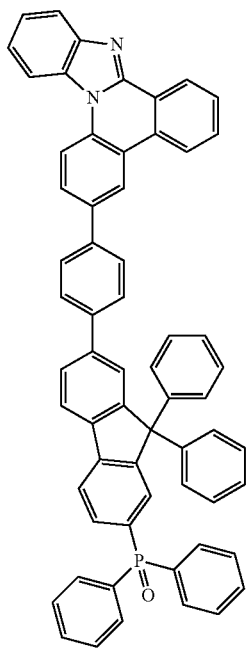
[Formula 1-45]
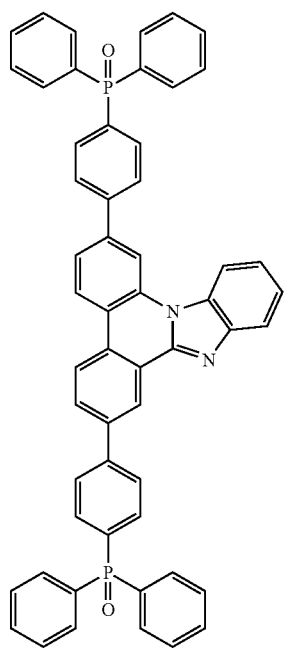
[Formula 1-44]
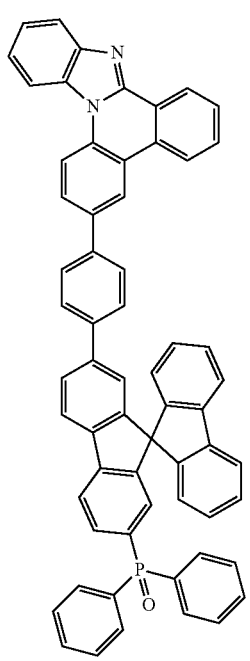
[Formula 1-46]

[Formula 1-47]
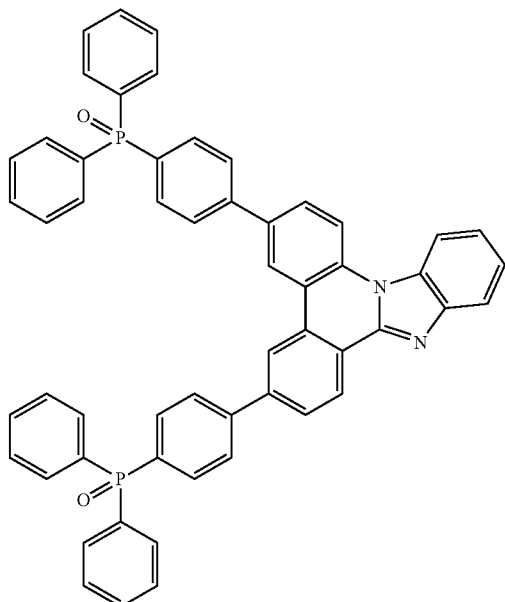
[Formula 1-48]
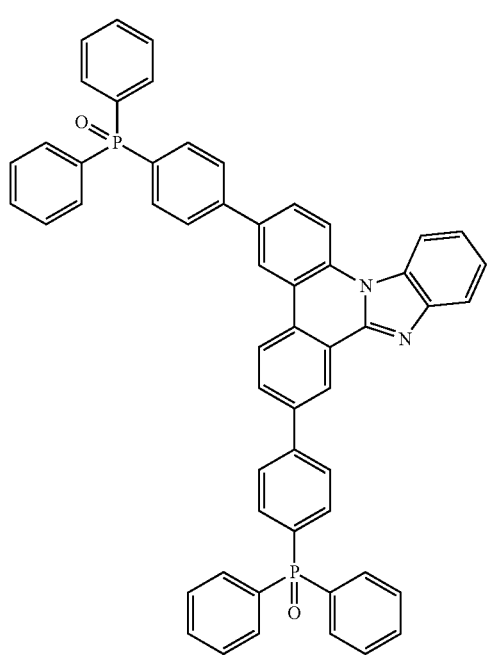
[Formula 1-49]
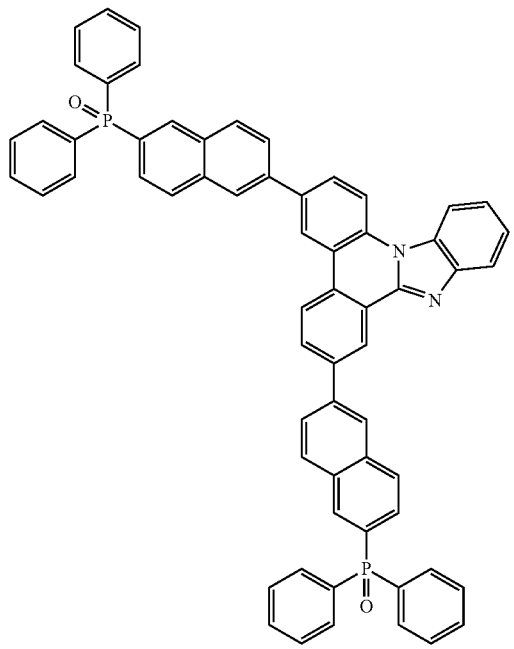
[Formula 1-50]
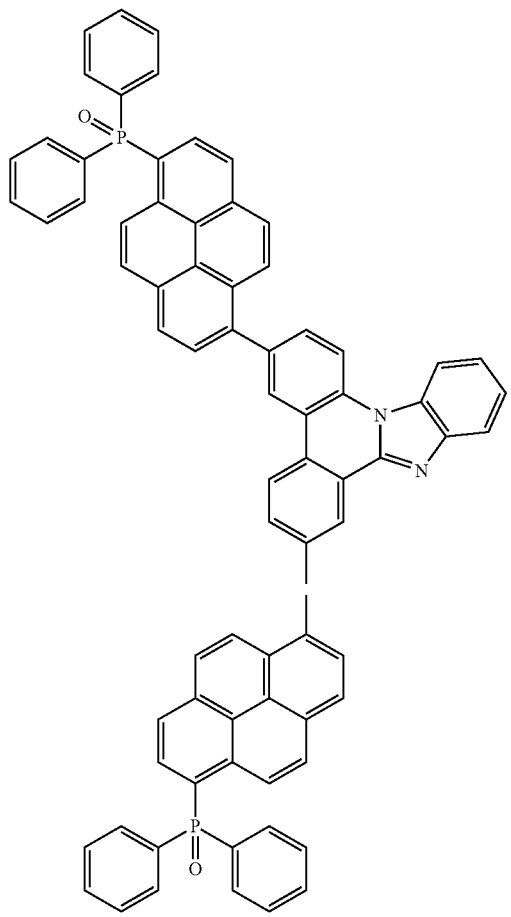
Hereinafter, a method of preparing the compound represented by Formula 1 will be described.

The compound represented by Formula 1 may be prepared by using a general method known in the art, such as a condensation reaction and a Suzuki coupling reaction.

The compounds represented by Formula 1 may have properties suitable to be used in the organic layer used in the organic light emitting diode by introducing various substituents into a core structure represented by the aforementioned Formulas. The compound represented by Formula 1 may exhibit properties even though the compound is used in any layer of the organic light emitting diode, but particularly may have the following properties.

The compounds into which the substituted or unsubstituted arylamine group is introduced are suitable for materials of a light emitting layer and a hole injection and hole transport layer, and the compounds into which the heterocyclic group comprising N is introduced are suitable for materials of an electron injection, an electron transport layer and a hole blocking layer.

The conjugation length of the compound has a close relationship with an energy band gap. Specifically, the energy band gap is reduced as the conjugation length of the compound increases. As described above, since the core of the compounds represented by Formula 1 comprises a limited conjugation, the core has properties from a small energy band gap to a large energy band gap.

In addition, compounds having intrinsic characteristics of the introduced substituent groups may be synthesized by introducing various substituent groups into the core structure as described above. For example, the material of the hole injection layer and the material of the hole transport layer used when the organic light emitting diode is manufactured may be a compound having the energy level that can transporting holes according to HOMO and can prevent electrons from moving from the light emitting layer according to LUMO. In particular, the core structure of the present compound may exhibit a stable property to the electrons, thus contributing to improving a life-span of the diode. The derivatives constituted by introducing substituents so as to be used in the materials of the light emitting layer and the electron transport layer may be prepared so that various arylamine-based dopants, aryl-based dopants, and dopants comprising metal have an appropriate energy band gap.

In addition, the energy band gap can be finely controlled, a property at an interface between organic materials can be improved, and the purpose of the material can become various by introducing various substituent groups into the core structure.

Meanwhile, since the compounds represented by Formula 1 have a high glass transition temperature (Tg), thermal stability is excellent. Such increase in thermal stability is an important factor providing driving stability to the diode.

In addition, an organic electronic diode according to the present invention is an organic electronic diode comprising a first electrode, a second electrode, and one or more organic layers interposed between the first electrode and the second electrode, and one or more layers of the organic layers comprise the compound represented by Formula 1.

The organic electronic diode according to the present invention may be manufactured by a preparation method and a material of a general organic electronic diode, except that one or more organic layers are formed by using the aforementioned compounds.

The compound of Formula 1 may be formed as the organic layer by a vacuum deposition method and a solution coating method when the organic electronic diode is manufactured. Herein, examples of the solution coating method comprise spin coating, dip coating, inkjet printing, screen printing, a spray method, roll coating and the like, but are not limited thereto.

The organic layer of the organic electronic diode of the present invention may be constituted by a single layer structure, but by a multilayered structure in which two or more organic layers are laminated. For example, the organic electronic diode of the present invention may have a structure comprising a hole injection layer, a hole transport layer, a light emitting layer, an electron transport layer, an electron injection layer and the like as an organic layer. However, the structure of the organic electronic diode is not limited thereto, but may comprise a smaller number of organic layers.

Accordingly, in the organic electronic diode of the present invention, the organic layer may comprise one or more layers of the hole injection layer, the hole transport layer, and a layer performing simultaneously hole injection and hole transporting, and one or more layers of the aforementioned layers may comprise the compound represented by Formula 1.

In addition, the organic layer may comprise the light emitting layer, and the light emitting layer may comprise the compound represented by Formula 1.

Further, the organic layer may comprise one or more layers of an electron transport layer, an electron injection layer, and a layer performing simultaneously electron transporting and electron injection, and one or more layers of the layers may comprise the compound represented by Formula 1.

In the organic layer having the multilayered structure, the compound of Formula 1 may be comprised in a light emitting layer, a layer performing simultaneously hole injection/hole transport and light emitting, a layer performing simultaneously hole transport and light emitting, a layer performing simultaneously electron transport and light emitting or the like.

For example, the structure of the organic light emitting diode of the present invention may have a structure shown in FIGS. 1 to 4, but is not limited thereto.

FIG. 1 illustrates an example of an organic light emitting diode having a structure where an anode 102, a light emitting layer 105 and a cathode 107 are sequentially laminated on a substrate 101. In the aforementioned structure, the compound of Formula 1 may be comprised in the light emitting layer 105.

FIG. 2 illustrates an example of an organic light emitting diode having a structure where an anode 102, hole injection/hole transport and light emitting layers 105, an electron transport layer 106 and a cathode 107 are sequentially laminated on a substrate 101. In the aforementioned structure, the compound of Formula 1 may be comprised in the hole injection/hole transport and light emitting layers 105.

FIG. 3 illustrates an example of an organic light emitting diode having a structure where a substrate 101, an anode 102, a hole injection layer 103, hole transport and light emitting layers 105, an electron transport layer 106 and a cathode 107 are sequentially laminated. In the aforementioned structure, the compound of Formula 1 may be comprised in the hole injection/hole transport and light emitting layers 105.

FIG. 4 illustrates an example of an organic light emitting diode having a structure where a substrate 101, an anode 102, a hole injection layer 103, a hole transport layer 104, electron transport and light emitting layers 105, and a cathode 107 are sequentially laminated. In the aforementioned structure, the compound of Formula 1 may be comprised in the electron transport and light emitting layers 105.

In the organic electronic diode of the present invention, it is more preferable that the compound represented by Formula 1 be comprised in the electron transport layer, the layer performing simultaneously electron transporting and electron injection or the light emitting layer.

For example, the organic light emitting diode according to the present invention may be manufactured by forming an anode by depositing metal or metal oxides having conductivity or an alloy thereof on a substrate by using a PVD (physical vapor deposition) method such as sputtering or e-beam evaporation, forming the organic layer comprising the hole injection layer, the hole transport layer, the light emitting layer and the electron transport layer thereon, and depositing the material that is capable of being used as a cathode thereon. In addition to this method, the organic light emitting diode may be manufactured by sequentially depositing a cathode material, an organic layer, and an anode material on a substrate.

The organic layer may have a multilayered structure comprising a hole injection layer, a hole transport layer, a light emitting layer, an electron transport layer and the like, but is not limited thereto and may have a single layer structure. Further, the organic layer may be manufactured in the smaller number of layers by using various polymer materials and not by a deposition method but a solvent process, for example, a method such as spin coating, dip coating, doctor blading, screen printing, inkjet printing and a heat transferring method.

It is preferable that the anode material be, in general, the material having the large work function so as to smoothly perform hole injection into the organic layer. Specific examples of the anode material that is capable of being used in the present invention comprise metal such as vanadium, chrome, copper, zinc, and gold, or an alloy thereof; metal oxides such as zinc oxides, indium oxides, indium tin oxides (ITO) and indium zinc oxides (IZO); a combination of metal and oxides such as ZnO:Al or $SnO_2$:Sb; and conductive polymers such as poly(3-methyl compound), poly[3,4-(ethylene-1,2-dioxy) compound](PEDT), polypyrole and polyaniline, but are is not limited thereto.

It is preferable that the cathode material be, in general, the material having the small work function so as to easily perform electron injection into the organic layer. Specific examples of the cathode material comprise metal such as magnesium, calcium, sodium, potassium, titanium, indium, yttrium, lithium, gadolinium, aluminum, silver, tin, and lead or an alloy thereof; a multilayered structure material such as LiF/Al or $LiO_2$/Al and the like, but are not limited thereto.

The hole injection material is a material that is capable of receiving holes well from the anode at a low voltage, and it is preferable that the HOMO (highest occupied molecular orbital) of the hole injection material be between the work function of the anode material and the HOMO of the organic layer therearound. Specific examples of the hole injection material comprise metal porphyrine, oligo thiophene, arylamine-based organic material, hexanitrilehexaazatriphenylene-based organic material, quinacridone-based organic material, perylene-based organic material, anthraquinone and polyaniline, polycompound-based conductive polymers and the like, but are not limited thereto.

The hole transport material is a material that is capable of receiving the holes from the anode or the hole injection layer and transferring the holes to the light emitting layer, and is preferably the material having the large mobility to the holes. Specific examples thereof comprise arylamine-based organic material, a conductive polymer, a block copolymer in which a conjugate portion and a non-conjugate portion are present together and the like, but are not limited thereto.

The light emitting material is a material that receives the holes and the electrons from the hole transport layer and the electron transport layer and combines the holes and the electrons to emit light in a visible ray region, and is preferably the material having excellent photon efficiency to fluorescence or phosphorescence. Specific examples thereof comprise a 8-hydroxy-quinoline aluminum complex ($Alq_3$); a carbazole-based compound; a dimerized styryl compound; BAlq; 10-hydroxybenzoquinoline-metal compound; a benzoxazole, benzthiazole and benzimidazole-based compound; a poly(p-phenylenevinylene) (PPV)-based polymer; a Spiro compound; polyfluorene, lubrene and the like, but are not limited thereto.

The electron transport material is a material that is capable of receiving the electrons well from the cathode and transferring the electrons to the light emitting layer, and is preferably the material having the large mobility to the electrons. Specific examples thereof comprise a 8-hydroxyquinoline Al complex; a complex comprising $Alq_3$; an organic radical compound; a hydroxyflavone metal complex and the like, but are not limited thereto.

The organic light emitting diode according to the present invention may be a top emission type, a bottom emission type, or a both-sided emission type according to the used material.

The compound according to the present invention may be applied to an organic electronic diode such as an organic solar cell, an organic photoconductor and an organic transistor by the principle that is similar to the principle applied to the organic light emitting diode.

Accordingly, the organic electronic diode may be selected from the group consisting of an organic light emitting diode, an organic phosphorescent diode, an organic solar cell, an organic photoconductor (OPC) and an organic transistor.

MODE FOR INVENTION

A better understanding of the present invention may be obtained in light of the following Examples which are set forth to illustrate, but are not to be construed to limit the present invention.

Example

<Preparation Example 1> Synthesis of the Compound of the Following Formula 1-1

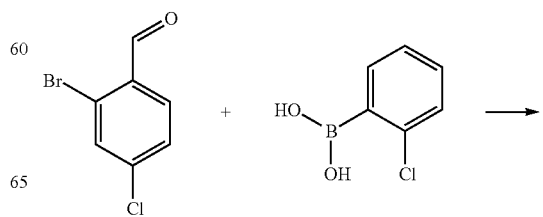

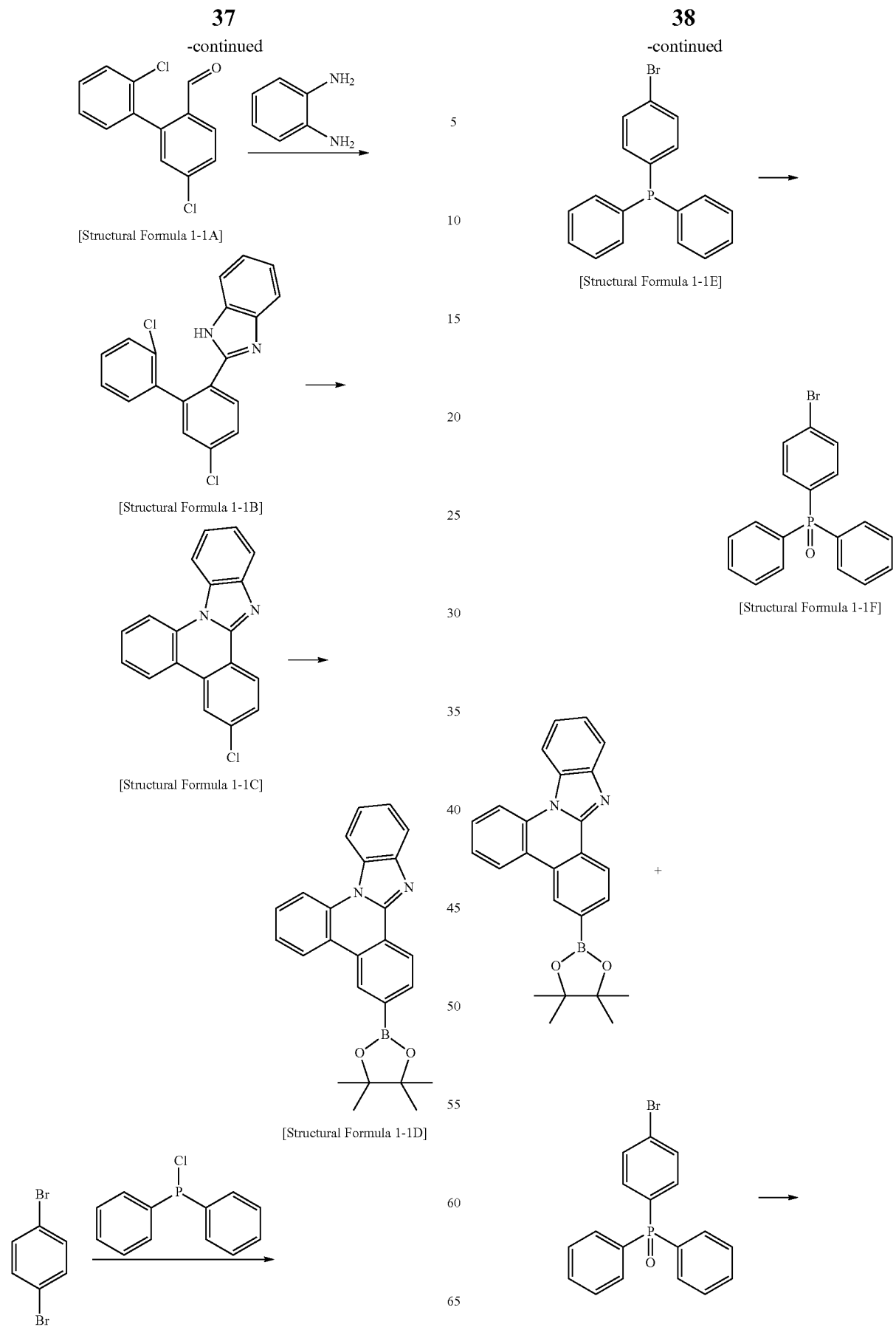

-continued

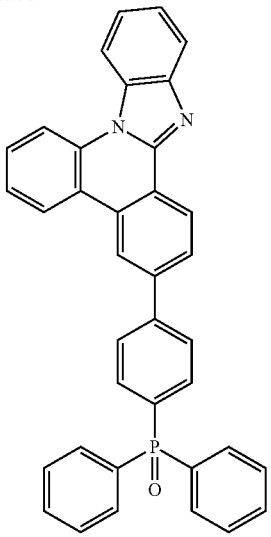

[Formula 1-1]

Preparation of Structural Formula 1-1A 2-bromo-4-chlorobenzaldehyde (11 g, 50 mmol) and 2-chlorophenylboronic acid (7.8 g, 50 mmol) were dissolved in tetrahydrofurane (100 ml), and then heated, and 100 ml of 2M potassium carbonate aqueous solution and Pd(PPh$_3$)$_4$ (0.5 g, 0.5 mmol) were added thereto, and agitated for 12 hours. After the temperature was decreased to normal temperature, the water layer was removed and the solvent of the organic layer was removed to obtain Structural Formula 1-1A (12 g, yield 96%) of brown oil.

MS: [M+1-1]$^+$=251

Preparation of Structural Formula 1-1B

Structural Formula 1-1A (12 g, 48 mmol) and 1,2-diaminobenzene (6.2 g, 57 mmol) were dissolved in ethanol (200 ml), and the solution where Na$_2$S$_2$O$_5$ (10.9 g, 57 mmol) was dissolved in water (20 ml) was added thereto, and heated and agitated for 6 hours. After cooling was performed to normal temperature, water (300 ml) was added, and the generated solid was filtered to obtain Structural Formula 1-1B (14 g, yield 84%).

MS: [M+H]$^+$=339

Preparation of Structural Formula 1-1C

Structural Formula 1-1B (14 g, 41 mmol) and Na$^t$BuO (4 g, 41 mmol) were dissolved in dimethylacetamide (200 ml) and then heated. After agitation was performed for 3 hours, cooling was performed to normal temperature, ethanol was added, and the generated solid was filtered to obtain Structural Formula 1-1C (12 g, yield 95%).

MS: [M+H]$^+$=305

Preparation of Structural Formula 1-1D

After Structural Formula 1-1C (12 g, 40 mmol), bis(pinacolato)diboron (12 g, 47 mmol) and acetate potassium (12 g, 118 mmol) were dissolved in dioxane (150 mL), the temperature was increased to 50° C., and Pd(DBA)$_2$ (0.23 g, 0.4 mmol) and P(Cy)$_3$ (0.22 g, 0.8 mmol) were added thereto, heated and agitated for 12 hours. After the reaction solution was cooled to room temperature, distilled water (100 mL) was added thereto, and extraction was performed with methylene chloride (100 mL×3). The organic layer was concentrated and recrystallized by ethanol to obtain Structural Formula 1-1D (14 g, yield 90%).

MS: [M+H]$^+$=397

Preparation of Structural Formula 1-1E

Dibromobenzene (20 g, 85 mmol) was dissolved in tetrahydrofurane (100 ml), and then cooled to −78° C. After n-BuLi (2.5 M, 37 ml, 93 mmol) was slowly applied in drops, agitation was performed for 30 min. Chlorodiphenylphosphine (17 g, 76 mmol) was slowly applied in drops, and then agitated for 3 hours, the temperature was increased to normal temperature, water (100 ml) was added thereto, and extraction was performed by tetrahydrofurane. The organic layer was concentrated and recrystallized by hexane to obtain Structural Formula 1-1E (20 g, yield 70%).

MS: [M+H]$^+$=342

Preparation of Structural Formula 1-1F

After Structural Formula 1-1E (20 g, 58 mmol) was dissolved in trichloromethane (200 ml), hydrogen peroxide (20 ml) was added thereto, and agitated for 12 hours. After water was removed by adding MgSO$_4$ and performing agitation, concentration was performed by filtration and recrystallization was performed by hexane to obtain Structural Formula 1-1F (18 g, yield 85%).

MS: [M+H]$^+$=358

Preparation of Formula 1-1

After Structural Formula 1-1D (8.9 g, 22.4 mmol) and Structural Formula 1-1F (8 g, 22.4 mmol) were completely dissolved in tetrahydrofurane (200 ml) by heating, 100 ml of 2M potassium carbonate aqueous solution and Pd(PPh$_3$)$_4$ (0.26 g, 0.22 mmol) were added and agitated for 12 hours. After the temperature was decreased to normal temperature, the water layer was removed and the generated solid was filtered. The filtered solid was recrystallized with tetrahydrofurane and acetone to obtain Formula 1-1 (8 g, yield 65%).

MS: [M+H]$^+$=545

<Preparation Example 2> Synthesis of the Compound of the Following Formula 1-2

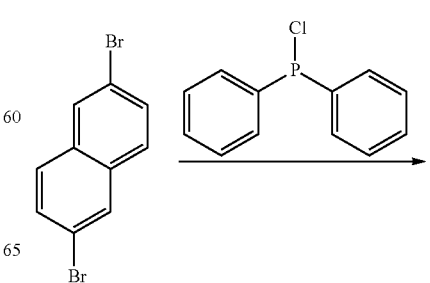

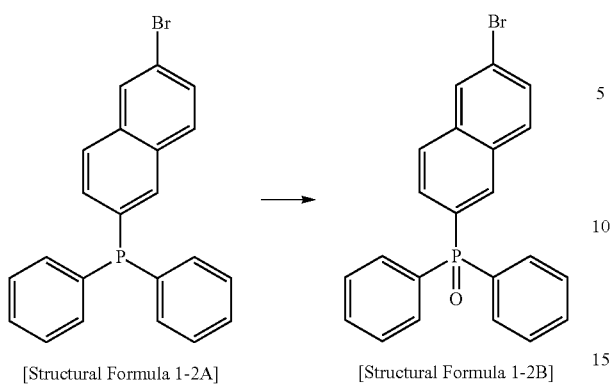

[Structural Formula 1-2A] → [Structural Formula 1-2B]

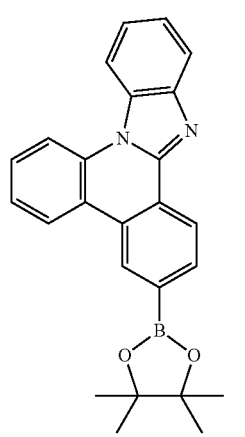

+

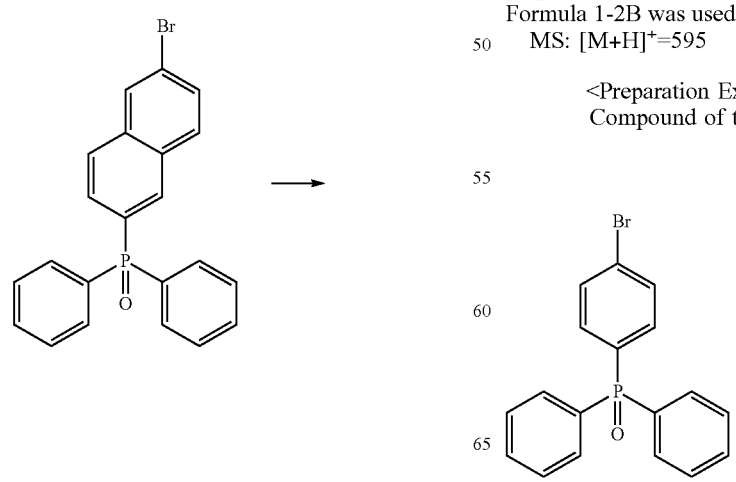

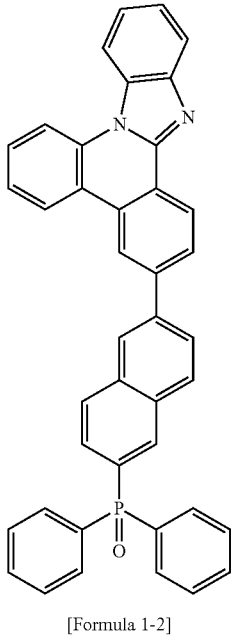 [SMILES: O=P(c1ccccc1)(c1ccccc1)c1ccc2cc(-c3ccc4c(c3)c3ccccc3n3c5ccccc5nc43)ccc2c1]

[Formula 1-2]

Preparation of Structural Formula 1-2A

Structural Formula 1-2A was obtained by the same method as the preparation method of Structural Formula 1-1E, except that 2,6-dibromonaphthalene was used instead of 1,4-dibromobenzene.

MS: [M+H]$^+$=392

Preparation of Structural Formula 1-2B

Structural Formula 1-2B was obtained by the same method as the preparation method of Structural Formula 1-1F, except that Structural Formula 1-2A was used instead of Structural Formula 1-1E.

MS: [M+H]$^+$=408

Preparation of Formula 1-2

Formula 1-2 was obtained by the same method as the preparation method of Formula 1-1, except that Structural Formula 1-2B was used instead of Structural Formula 1-1F.

MS: [M+H]$^+$=595

<Preparation Example 3> Synthesis of the Compound of the Following Formula 1-3

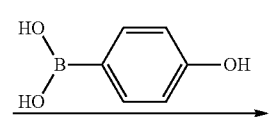

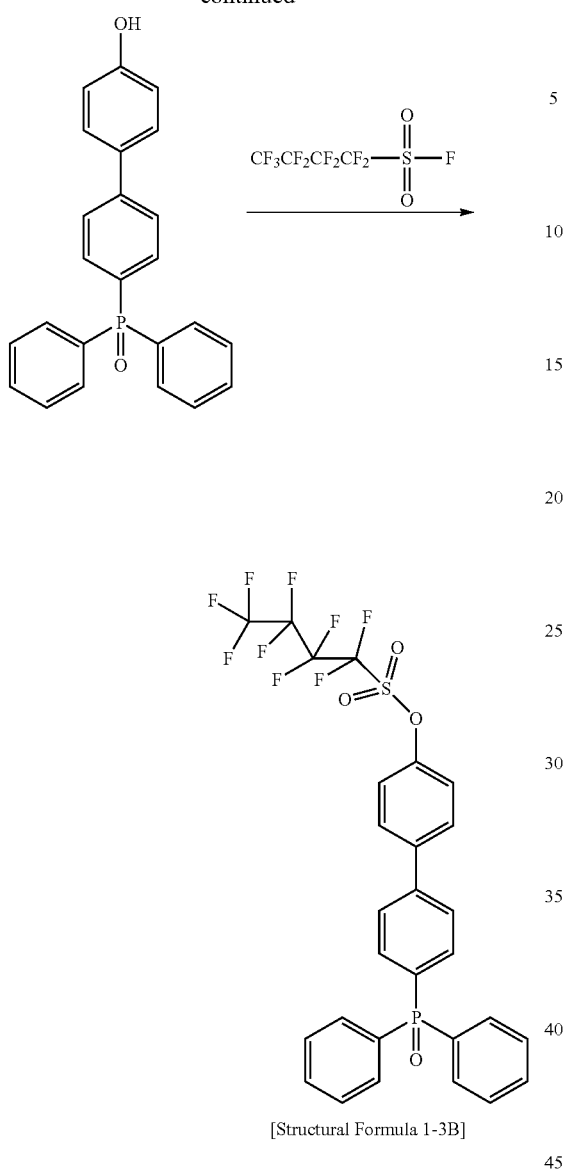

[Structural Formula 1-3B]

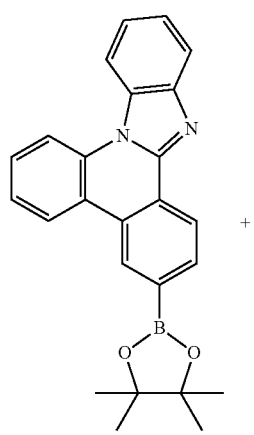

+

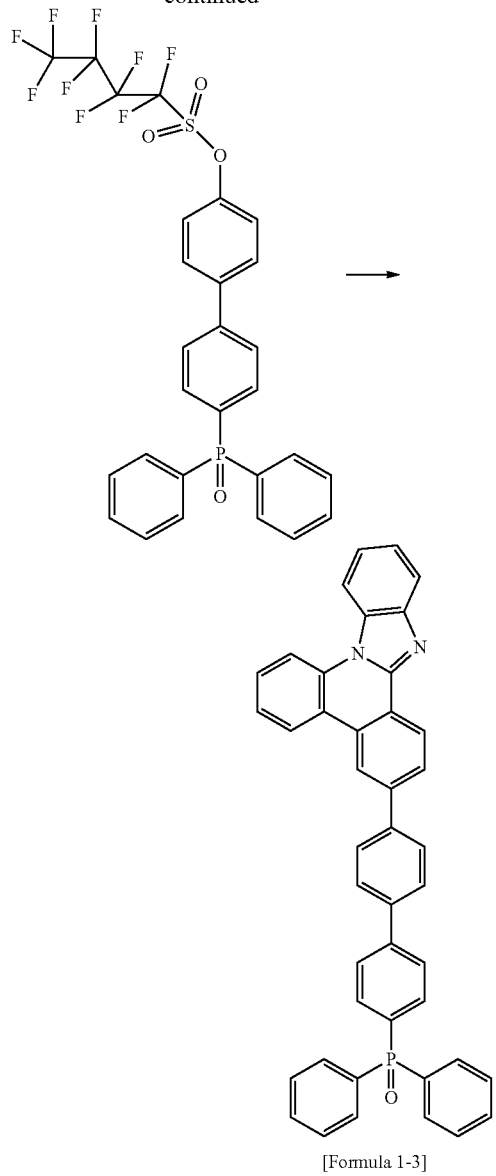

[Formula 1-3]

Preparation of Structural Formula 1-3A

After Structural Formula 1-1F (8 g, 22.4 mmol) and 4-hydroxyphenylboronic acid (3.1 g, 22.4 mmol) were completely dissolved in tetrahydrofurane (200 ml) by heating, 100 ml of 2M potassium carbonate aqueous solution and Pd(PPh$_3$)$_4$ (0.26 g, 0.22 mmol) were added and agitated for 12 hours. After the temperature was decreased to normal temperature, the organic layer was extracted, and the generated solid was filtered by blowing up the solvent. The filtered solid was recrystallized with tetrahydrofurane and hexane to obtain Structural Formula 1-3A (7 g, yield 84%). MS: [M+H]$^+$=371

Preparation of Structural Formula 1-3B

After Structural Formula 1-3A (7 g, 18.9 mmol) was dissolved in acetonitrile (200 ml), perchlorobutanesulfonyl fluoride (2.9 g, 20.8 mmol) and 100 ml of 2M potassium carbonate aqueous solution were added, heated and agitated for 12 hours. After the temperature was decreased to normal temperature, the organic layer was extracted, and the generated solid was filtered by blowing up the solvent. The filtered solid was recrystallized with chloroform and hexane to obtain Structural Formula 1-3B (9.5 g, yield 75%).

MS: [M+H]$^+$=653

Preparation of Formula 1-3

Formula 1-3 was obtained by the same method as the preparation method of Formula 1-1, except that Structural Formula 1-3B was used instead of Structural Formula 1-1F.

MS: [M+H]$^+$=621

<Preparation Example 4> Synthesis of the Compound of the Following Formula 1-4

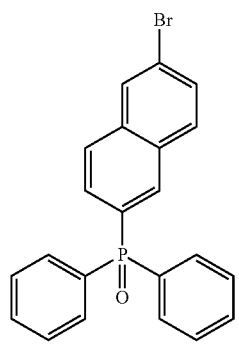
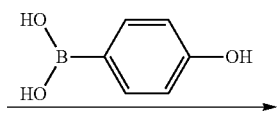
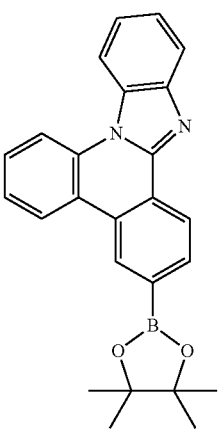

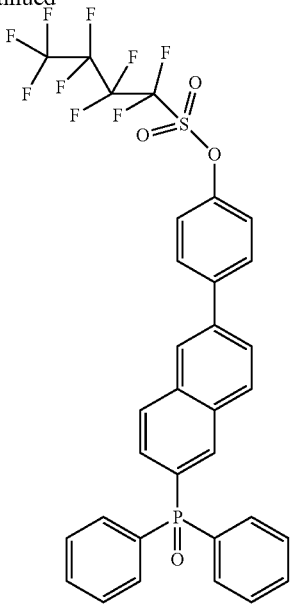

[Structural Formula 1-4B]

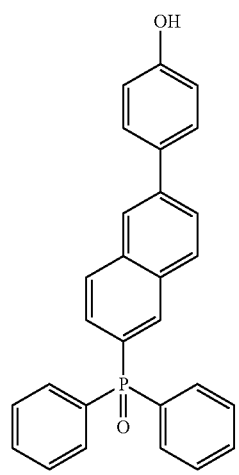

[Structural Formula 1-4A]

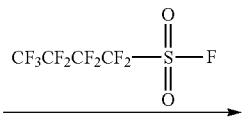
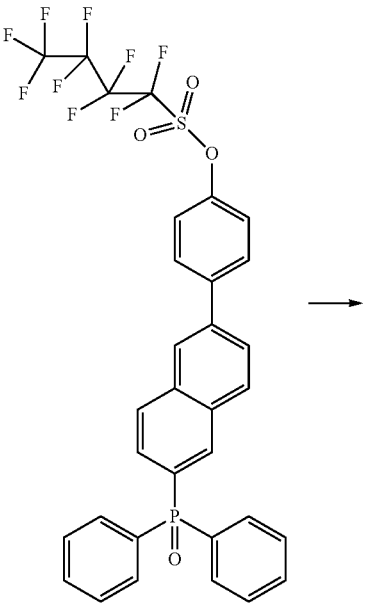

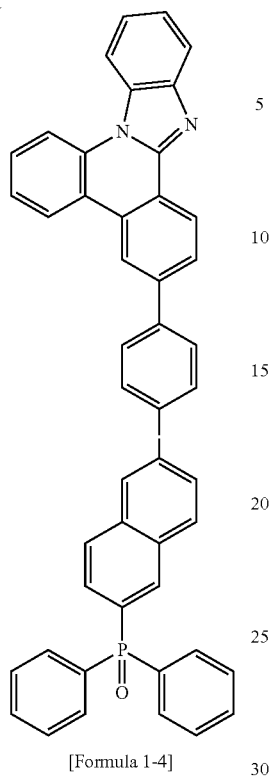

[Formula 1-4]

Preparation of Structural Formula 1-4A

Structural Formula 1-4A was obtained by the same method as the preparation method of Structural Formula 1-3A, except that Structural Formula 1-2B was used instead of Structural Formula 1-1F.
MS: [M+H]$^+$=421

Preparation of Structural Formula 1-4B

Structural Formula 1-4B was obtained by the same method as the preparation method of Structural Formula 1-3B, except that Structural Formula 1-4A was used instead of Structural Formula 1-3A.
MS: [M+H]$^+$=703

Preparation of Formula 1-4

Formula 1-4 was obtained by the same method as the preparation method of Formula 1-1, except that Structural Formula 1-4B was used instead of Structural Formula 1-1F.
MS: [M+H]$^+$=671

<Preparation Example 5> Synthesis of the Compound of the Following Formula 1-5

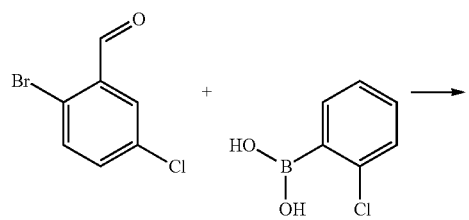

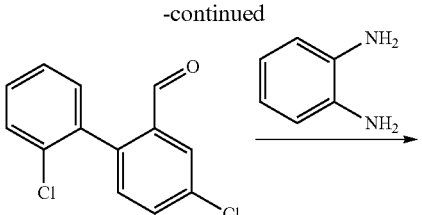

[Structural Formula 1-5A]

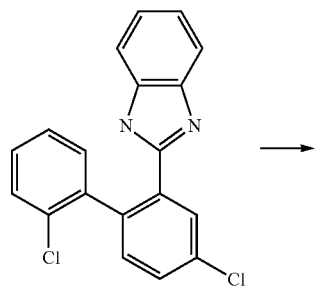

[Structural Formula 1-5B]

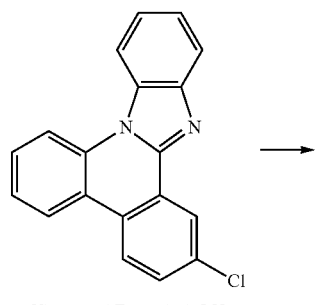

[Structural Formula 1-5C]

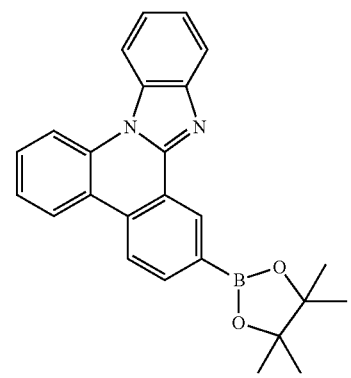

[Structural Formula 1-5D]

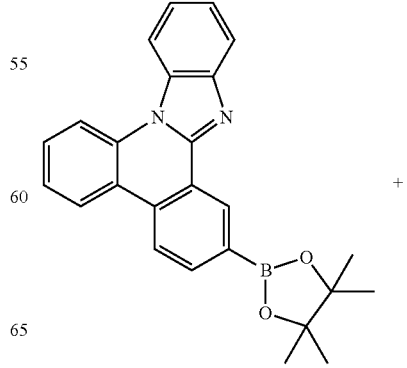

+

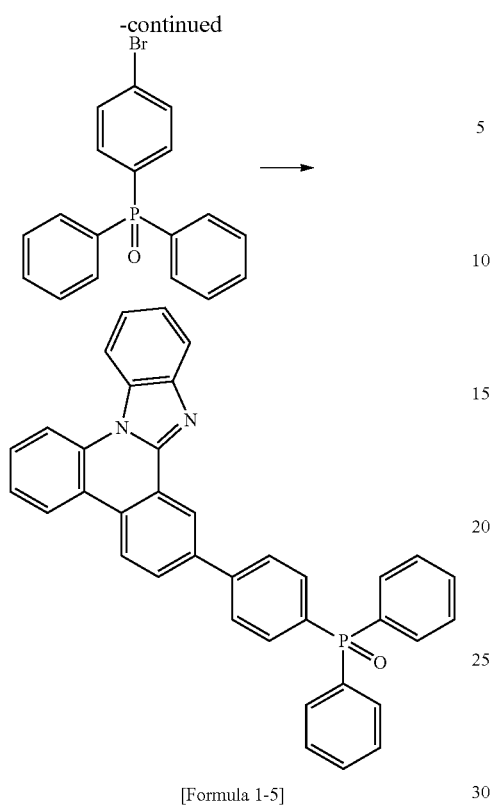

[Formula 1-5]

Preparation of Structural Formula 1-5A

Structural Formula 1-5A was obtained by the same method as the preparation method of Structural Formula 1-1A, except that 2-bromo-5-chlorobenzaldehyde was used instead of 2-bromo-4-chlorobenzaldehyde.
MS: $[M+H]^+=251$ Preparation of Structural Formula 1-5B Structural Formula 1-5B was obtained by the same method as the preparation method of Structural Formula 1-1B, except that Structural Formula 1-5A was used instead of Structural Formula 1-1A.
MS: $[M+H]^+=339$ Preparation of Structural Formula 1-5C Structural Formula 1-5C was obtained by the same method as the preparation method of Structural Formula 1-1C, except that Structural Formula 1-5B was used instead of Structural Formula 1-1B.
MS: $[M+H]^+=303$ Preparation of Structural Formula 1-5D Structural Formula 1-5D was obtained by the same method as the preparation method of Structural Formula 1-1D, except that Structural Formula 1-5C was used instead of Structural Formula 1-1C.
MS: $[M+H]^+=395$ Preparation of Formula 1-5

Formula 1-5 was obtained by the same method as the preparation method of Formula 1-1, except that Structural Formula 1-5D was used instead of Structural Formula 1-1D.
MS: $[M+H]^+=545$ <Preparation Example 6> Synthesis of the Compound of the Following Formula 1-6

[Formula 1-6]

Preparation of Formula 1-6

Formula 1-6 was obtained by the same method as the preparation method of Formula 1-2, except that Structural Formula 1-5D was used instead of Structural Formula 1-1D.
MS: $[M+H]^+=595$

<Preparation Example 7> Synthesis of the Compound of the Following Formula 1-7
<Preparation Example 8> Synthesis of the Compound of the Following Formula 1-8
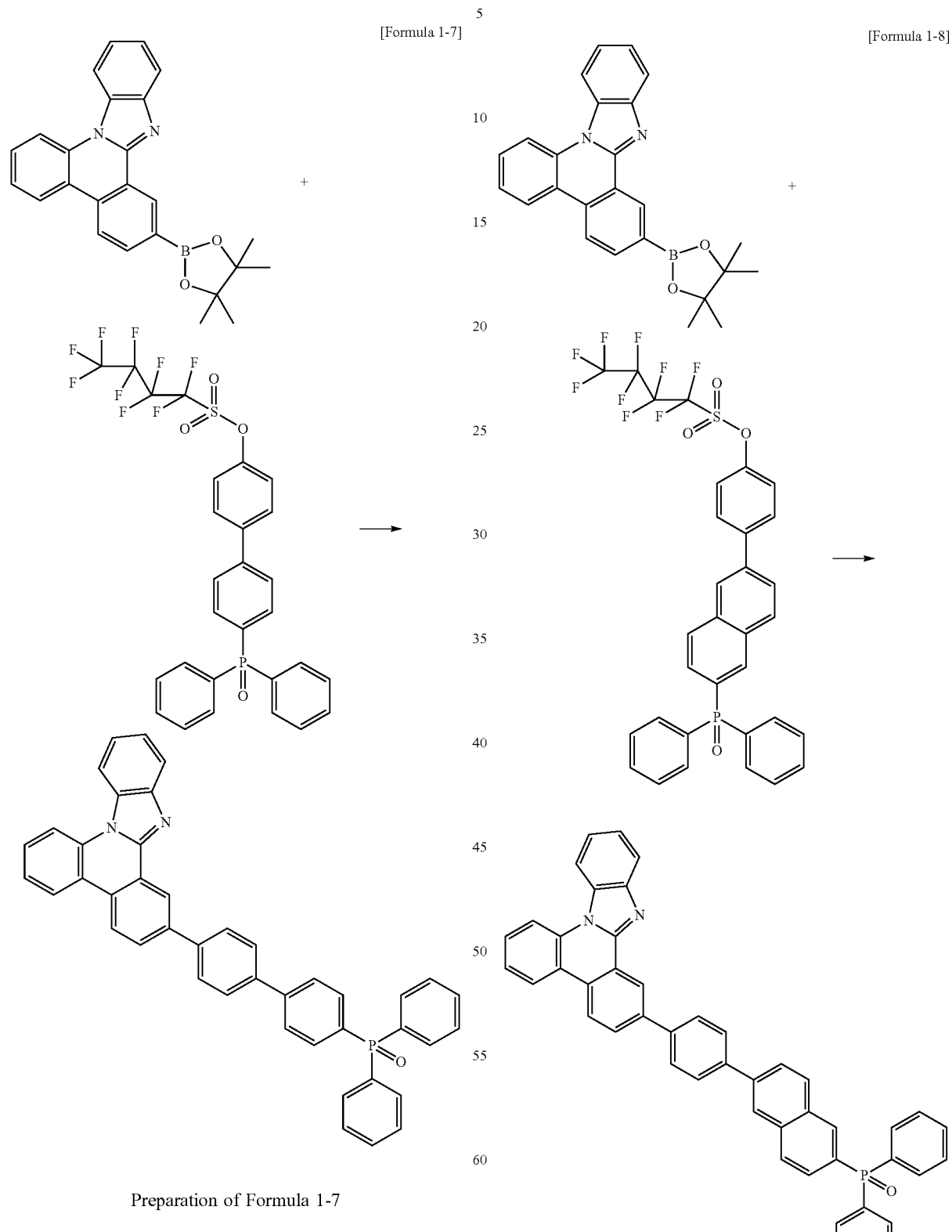
Preparation of Formula 1-7
Formula 1-7 was obtained by the same method as the preparation method of Formula 1-3, except that Structural Formula 1-5D was used instead of Structural Formula 1-1D.
MS: [M+H]$^+$=621

Preparation of Formula 1-8

Formula 1-8 was obtained by the same method as the preparation method of Formula 1-4, except that Structural Formula 1-5D was used instead of Structural Formula 1-1D.

MS: [M+H]⁺=671

<Preparation Example 9> Synthesis of the Compound of the Following Formula 1-9

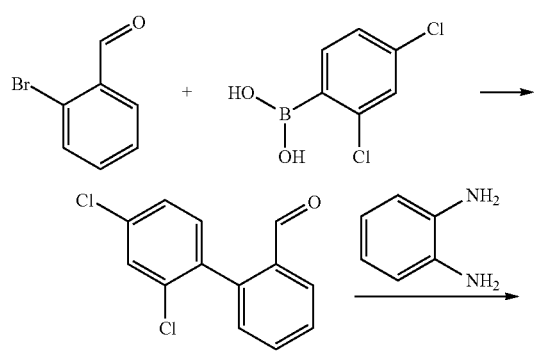

[Structural Formula 1-9A]

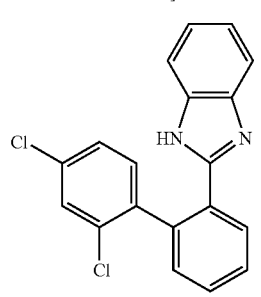

[Structural Formula 1-9B]

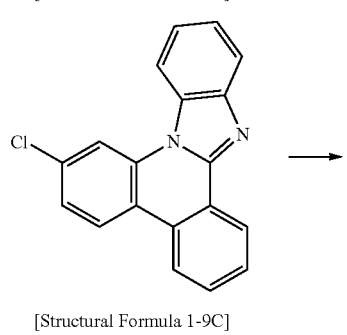

[Structural Formula 1-9C]

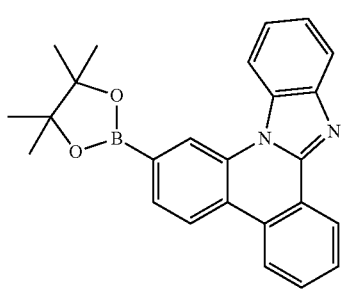

[Structural Formula 1-9D]

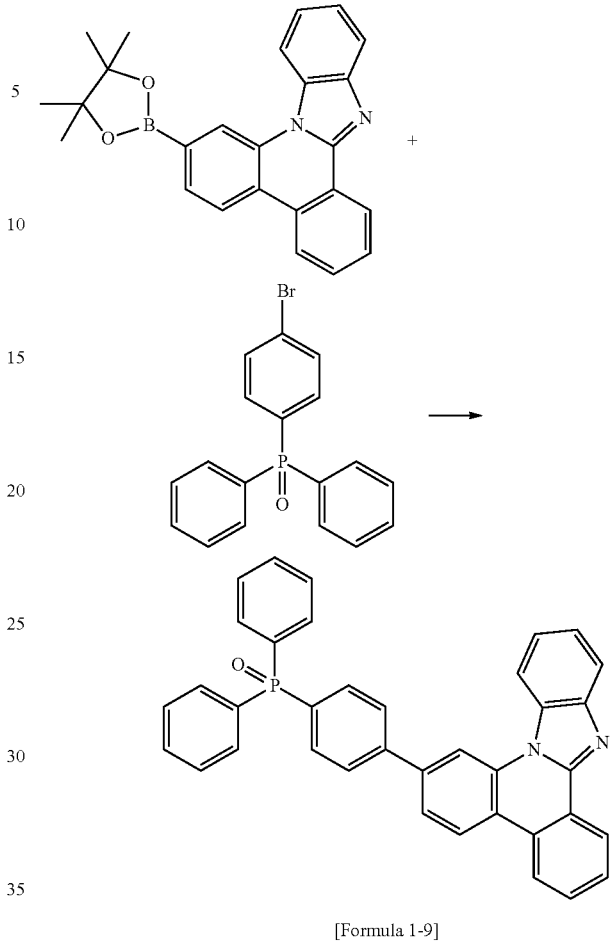

[Formula 1-9]

Preparation of Structural Formula 1-9A

Structural Formula 1-9A was obtained by the same method as the preparation method of Structural Formula 1-1A, except that 2,4-dichlorophenylboronic acid was used instead of 2-bromo-4-chlorobenzaldehyde and 2-bromobenzaldehyde 2-chlorophenylboronic acid.

MS: [M+H]⁺=251

Preparation of Structural Formula 1-9B

Structural Formula 1-9B was obtained by the same method as the preparation method of Structural Formula 1-1B, except that Structural Formula 1-9A was used instead of Structural Formula 1-1A.

MS: [M+H]⁺=339

Preparation of Structural Formula 1-9C

Structural Formula 1-9C was obtained by the same method as the preparation method of Structural Formula 1-1C, except that Structural Formula 1-9B was used instead of Structural Formula 1-1B.

MS: [M+H]⁺=303

Preparation of Structural Formula 1-9D

Structural Formula 1-9D was obtained by the same method as the preparation method of Structural Formula 1-1D, except that Structural Formula 1-9C was used instead of Structural Formula 1-1C.

MS: [M+H]⁺=395

Preparation of Formula 1-9

Formula 1-9 was obtained by the same method as the preparation method of Formula 1-1, except that Structural Formula 1-9D was used instead of Structural Formula 1-1D.

MS: [M+H]$^+$=545

<Preparation Example 10> Synthesis of the Compound of the Following Formula 1-10

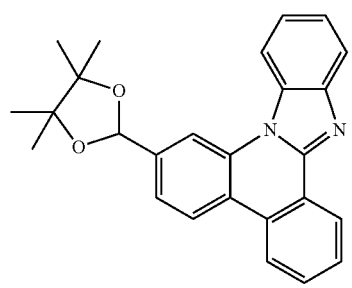

[Formula 1-10]

+

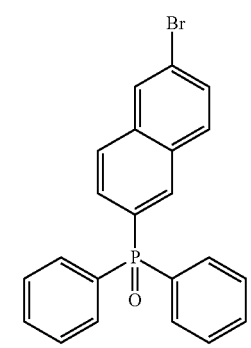

Preparation of Formula 1-10

Formula 1-10 was obtained by the same method as the preparation method of Formula 1-2, except that Structural Formula 1-9D was used instead of Structural Formula 1-1D.

MS: [M+H]$^+$=595

<Preparation Example 11> Synthesis of the Compound of the Following Formula 1-11

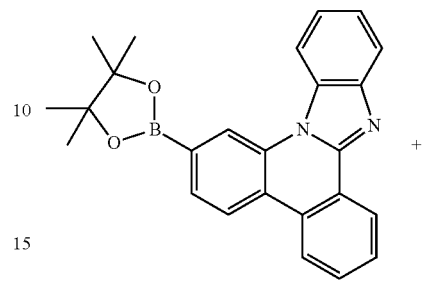

[Formula 1-11]

+

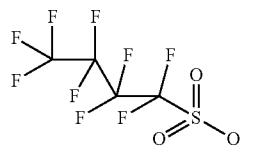

→

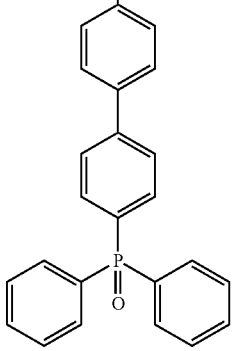

Preparation of Formula 1-11

Formula 1-11 was obtained by the same method as the preparation method of Formula 1-3, except that Structural Formula 1-9D was used instead of Structural Formula 1-1D.

MS: [M+H]$^+$=621

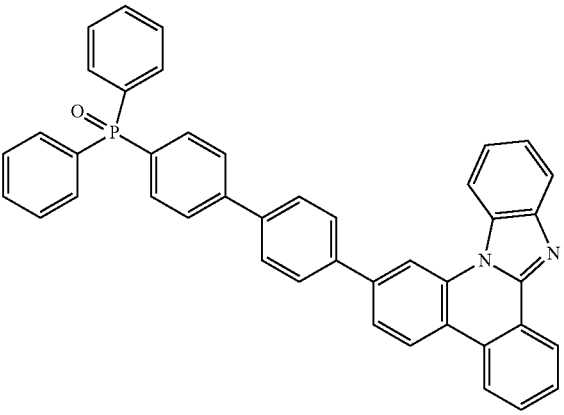

<Preparation Example 12> Synthesis of the Compound of the Following Formula 1-12

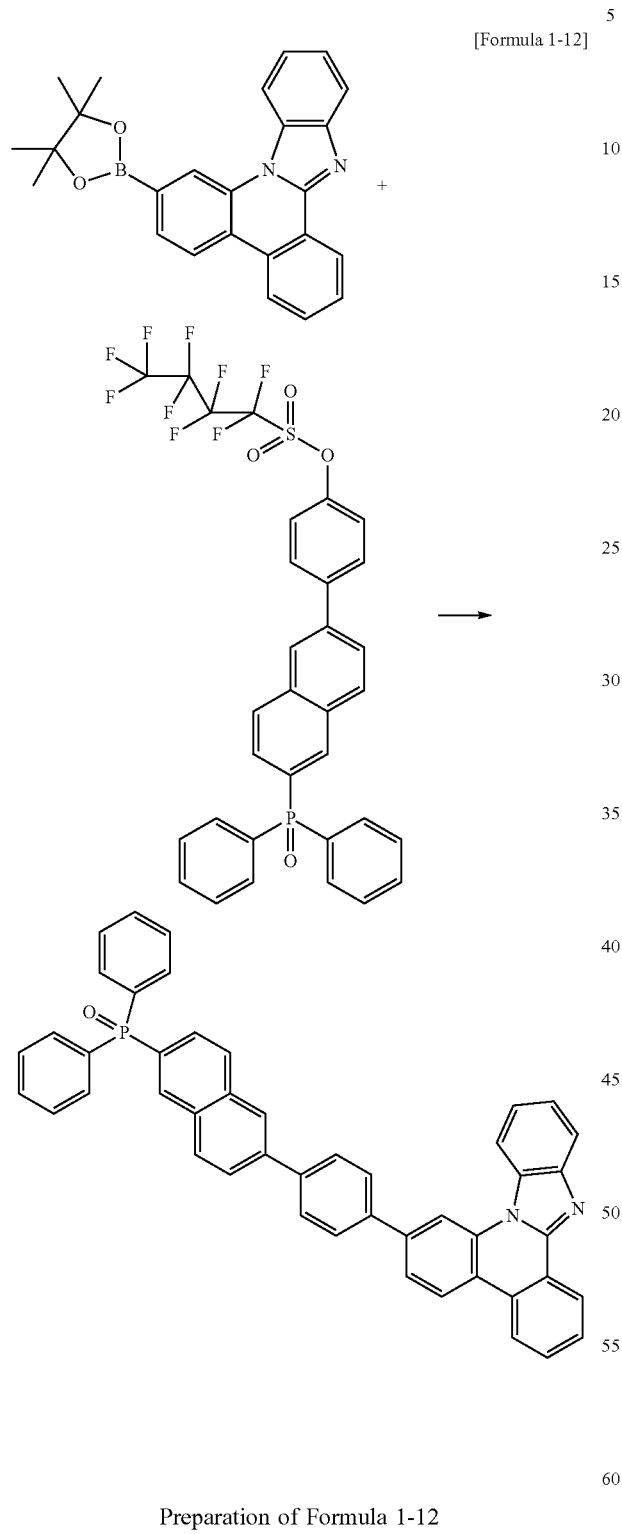

[Formula 1-12]

Preparation of Formula 1-12

Formula 1-12 was obtained by the same method as the preparation method of Formula 1-4, except that Structural Formula 1-9D was used instead of Structural Formula 1-1D.

MS: [M+H]$^+$=671

<Preparation Example 13> Synthesis of the Compound of the Following Formula 1-13

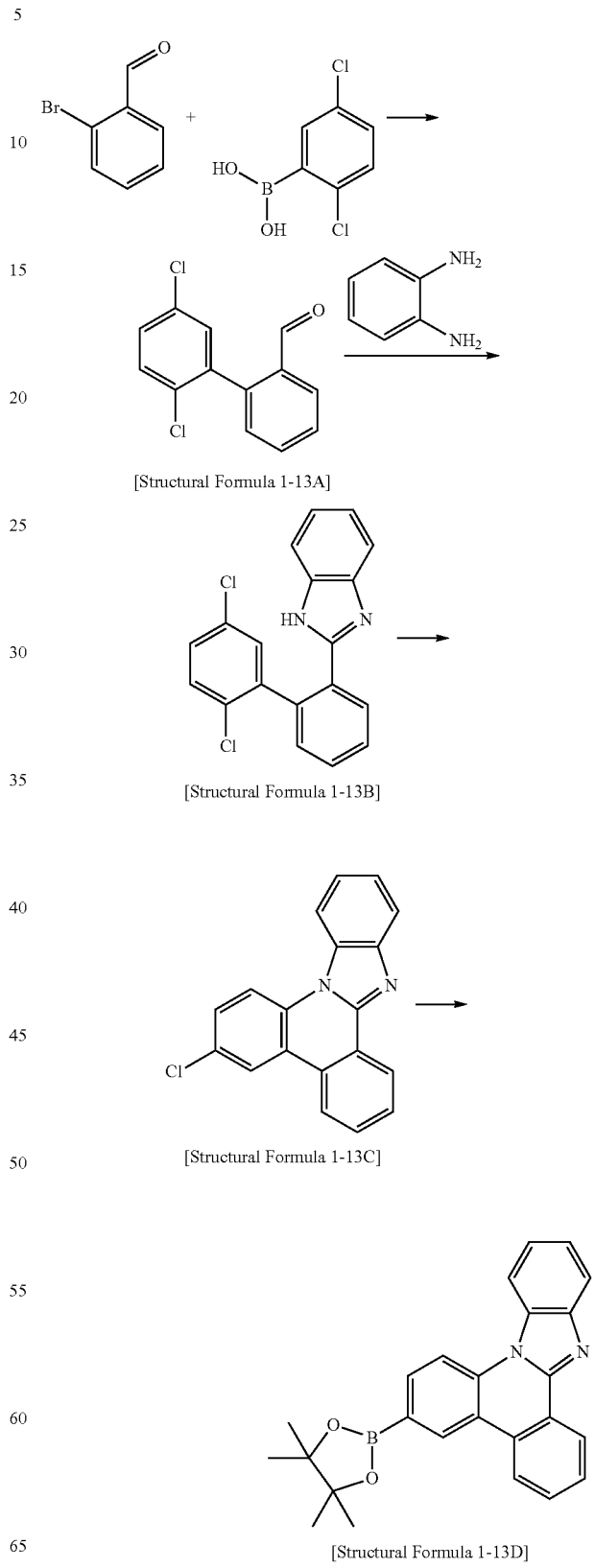

[Structural Formula 1-13A]

[Structural Formula 1-13B]

[Structural Formula 1-13C]

[Structural Formula 1-13D]

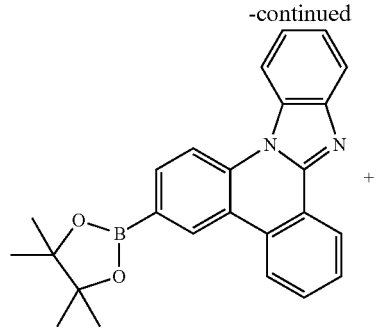

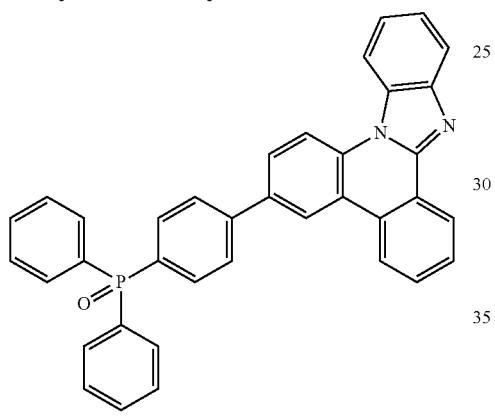

[Formula 1-13]

Preparation of Structural Formula 1-13A

Structural Formula 1-13A was obtained by the same method as the preparation method of Structural Formula 1-1A, except that 2,5-dichlorophenylboronic acid was used instead of 2-bromo-4-chlorobenzaldehyde and 2-bromobenzaldehyde 2-chlorophenylboronic acid.

MS: [M+H]$^+$=251

Preparation of Structural Formula 1-13B

Structural Formula 1-13B was obtained by the same method as the preparation method of Structural Formula 1-1B, except that Structural Formula 1-13A was used instead of Structural Formula 1-1A.

MS: [M+H]$^+$=339

Preparation of Structural Formula 1-13C

Structural Formula 1-13C was obtained by the same method as the preparation method of Structural Formula 1-1C, except that Structural Formula 1-13B was used instead of Structural Formula 1-1B.

MS: [M+H]$^+$=303

Preparation of Structural Formula 1-13D

Structural Formula 1-13D was obtained by the same method as the preparation method of Structural Formula 1-1D, except that Structural Formula 1-13C was used instead of Structural Formula 1-1C.

MS: [M+H]$^+$=395

Preparation of Formula 1-13

Formula 1-13 was obtained by the same method as the preparation method of Formula 1-1, except that Structural Formula 1-13D was used instead of Structural Formula 1-1D.

MS: [M+H]$^+$=545

<Preparation Example 14> Synthesis of the Compound of the Following Formula 1-14

[Formula 1-14]

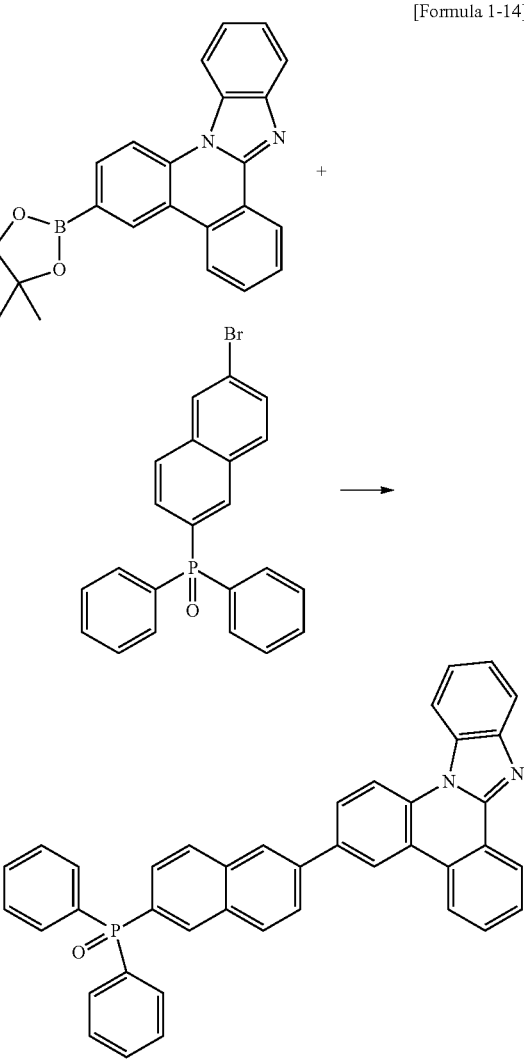

Preparation of Formula 1-14

Formula 1-14 was obtained by the same method as the preparation method of Formula 1-2, except that Structural Formula 1-13D was used instead of Structural Formula 1-1D.

MS: $[M+H]^+=595$

<Preparation Example 15> Synthesis of the Compound of the Following Formula 1-15

Preparation of Formula 1-15

Formula 1-15 was obtained by the same method as the preparation method of Formula 1-3, except that Structural Formula 1-13D was used instead of Structural Formula 1-1D.

MS: $[M+H]^+=621$

<Preparation Example 16> Synthesis of the Compound of the Following Formula 1-16

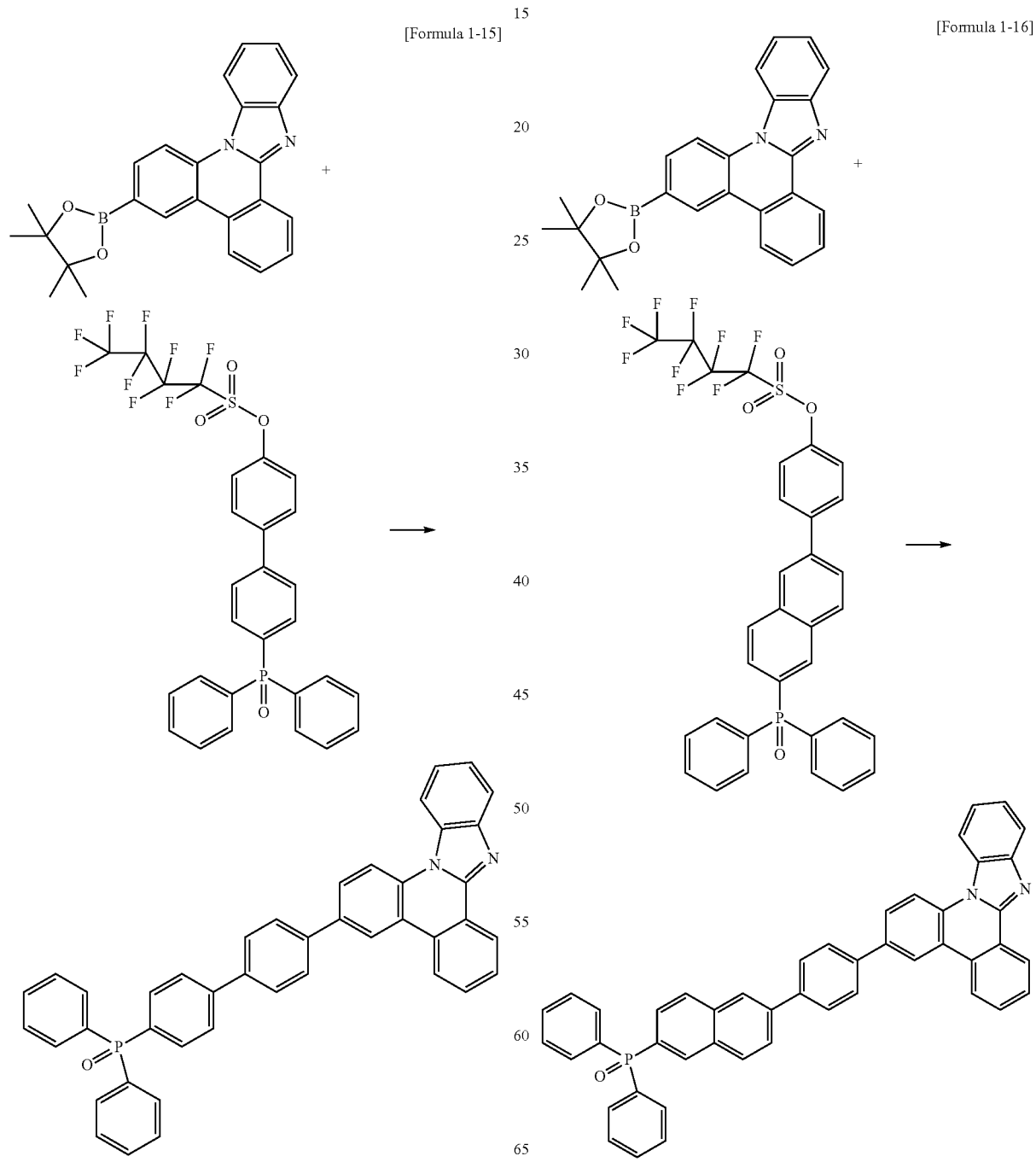

Preparation of Formula 1-16

Formula 1-16 was obtained by the same method as the preparation method of Formula 1-4, except that Structural Formula 1-13D was used instead of Structural Formula 1-1D.

MS: $[M+H]^+=671$

Example 1

A glass substrate (corning 7059 glass) on which a thin film of ITO (indium tin oxide) was applied to a thickness of 1000 Å was immersed in distilled water having a dispersing agent dissolved therein to be washed with ultrasonic waves. In this case, a product manufactured by Fisher Co. was used as the detergent, and the distilled water was one which had been twice filtered by a filter of the product manufactured by Millipore Co. ITO was washed for 30 minutes, and then washing with ultrasonic waves was repeated twice for 10 minutes by distilled water. After the completion of washing with distilled water, washing with ultrasonic waves was carried out by sequentially using solvents such as isopropyl alcohol, acetone and methanol, and the resultant product was dried.

Hexanitrile hexaazatriphenylene was applied to a thickness of 500 Å by thermal vacuum deposition on the ITO transparent electrode thus prepared to form a hole injecting layer. After NPB (400 Å) which was the material transporting the holes was deposited under the vacuum state thereon, the host H1 and the dopant D1 compound were deposited under the vacuum state to a thickness of 300 Å as a light emitting layer. Thereafter, the Formula 1-1 compound synthesized in Preparation Example 1 and LiQ were applied together by thermal vacuum deposition (200 Å) as electron injection and transport layers. Lithium quinolate (LiQ) in a thickness of 12 Å and aluminum in a thickness of 2,000 Å were subsequently deposited on the electron transport layer to form a cathode, thereby manufacturing the organic light emitting diode.

E1 was used as the Comparative Example of the electron transport layer.

In the aforementioned process, the deposition speed of the organic material was maintained at 1 Å/sec, the deposition speed of lithium quinolate was maintained at 0.2 Å/sec, and the deposition speed of aluminum was maintained at 3 to 7 Å/sec.

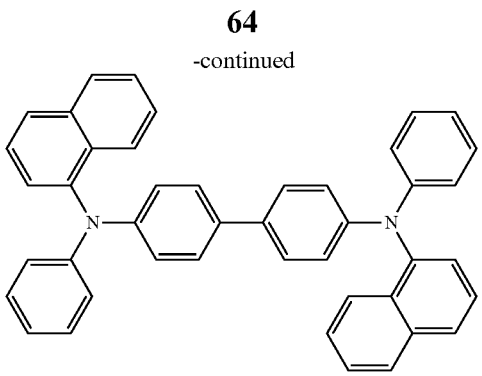

[NPB]

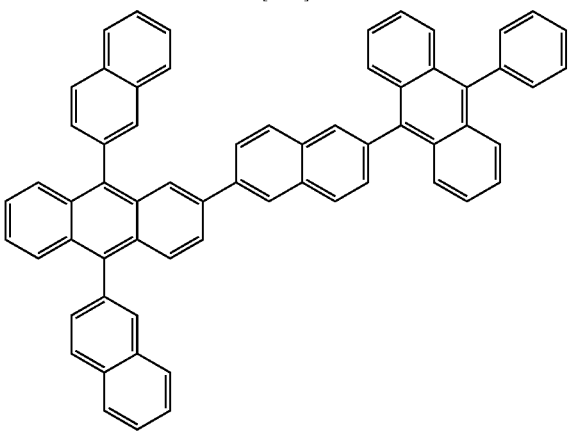

[H1]

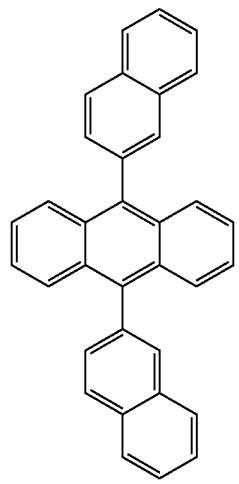

[H2]

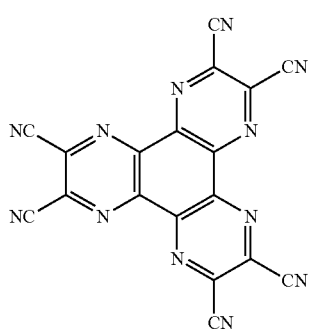

[hexanitrile hexaazatriphenylene]

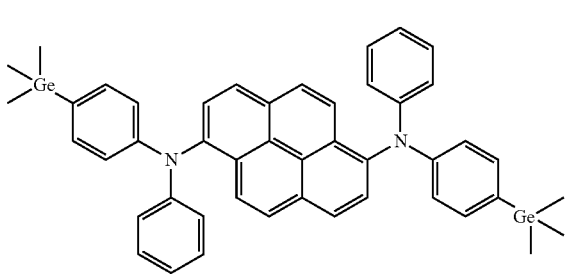

[D1]

-continued

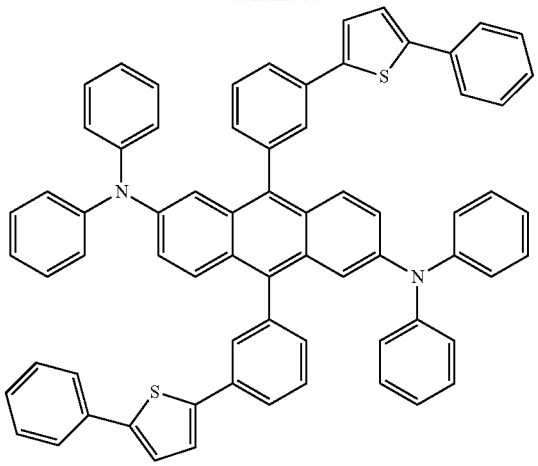

[D2]

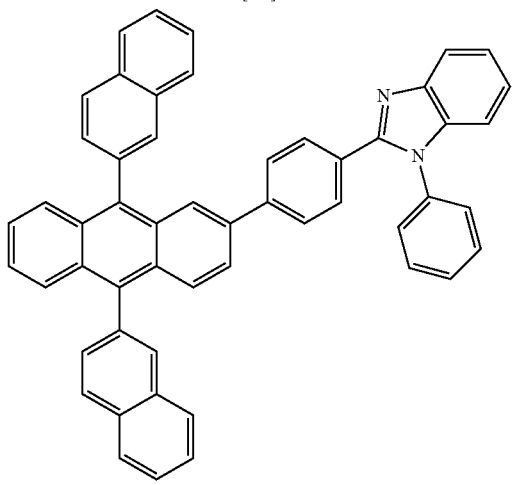

[E1]

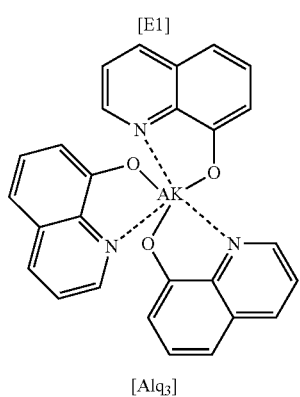

[Alq3]

Example 2

The same experiment was performed, except that Formula 1-5 was used instead of Formula 1-1 as the electron transport layer in Example 1.

Example 3

The same experiment was performed, except that Formula 1-7 was used instead of Formula 1-1 as the electron transport layer in Example 1.

Example 4

The same experiment was performed, except that Formula 1-8 was used instead of Formula 1-1 as the electron transport layer in Example 1.

Comparative Example 1

The same experiment was performed, except that E1 was used instead of Formula 1-1 as the electron transport layer in Example 1.

Like the aforementioned Examples, the experiment results of the organic light emitting diode manufactured by using the compounds as the electron transport layer material are described in Table 1.

TABLE 1

| Experimental Example (5 mA/cm²) | ETL material | Voltage (V) | Efficiency (cd/A) | Color coordinate (x, y) | Life-span (Td5) (hour) |
|---|---|---|---|---|---|
| Comparative Example 1 | E1 | 4.21 | 19.05 | (0.314, 0.650) | 94 |
| Example 1 | Formula 1-1 | 5.17 | 16.00 | (0.315, 0.650) | 498 |
| Example 2 | Formula 1-5 | 5.22 | 18.29 | (0.314, 0.655) | 150 |
| Example 3 | Formula 1-7 | 5.00 | 18.29 | (0.311, 0.654) | 366 |
| Example 4 | Formula 1-8 | 4.96 | 17.52 | (0.315, 0.655) | 366 |

As described above, the new compound according to the present invention may be used as the material of the organic layer of the organic light emitting diode and the organic electronic diode by introducing various substituent groups and the like. The organic light emitting diode and the organic electronic diode using the compound represented by Formula 1 according to the present invention as the material of the organic layer exhibit excellent efficiency, driving voltage, and life-span properties.

The invention claimed is:
1. An organic electronic diode which comprises a first electrode, a second electrode, and one or more organic layers interposed between the first electrode and the second electrode, wherein the one or more organic layers comprise an electron transport layer comprising a compound represented by Formula 2:

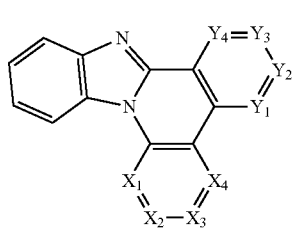

[Formula 2]

wherein
$X_1$ is CR3, $X_2$ is CR4, $X_3$ is CR5, $X_4$ is CR6, $Y_1$ is CR7, $Y_2$ is CR8, $Y_3$ is CR9, $Y_4$ is CR10,
R3, R6, R7, and R10 are each independently hydrogen, at least one of R4, R5, R8 and R9 is the group represented by Formula 1A, and the others are hydrogen,

[Formula 1A]

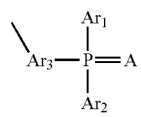

Ar₁ and Ar₂ are each independently an aryl group,

Ar₃ is an arylene group unsubstituted or substituted with an alkyl group or an aryl group.

2. The organic electronic diode of claim 1, wherein the organic electronic diode is an organic light emitting diode and an organic phosphorescent diode.

3. The compound of claim 1, wherein Ar₃ is an arylene group selected from the group consisting of following formulae:

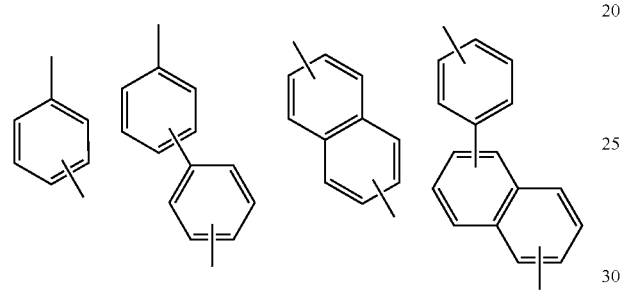

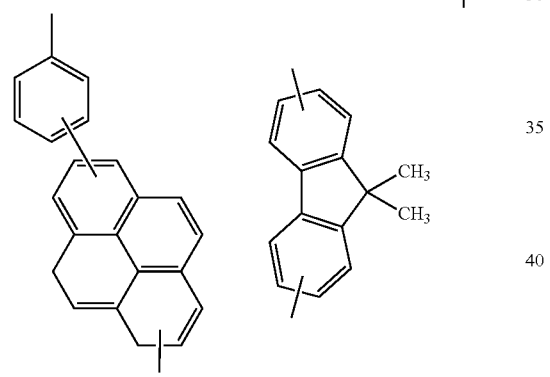

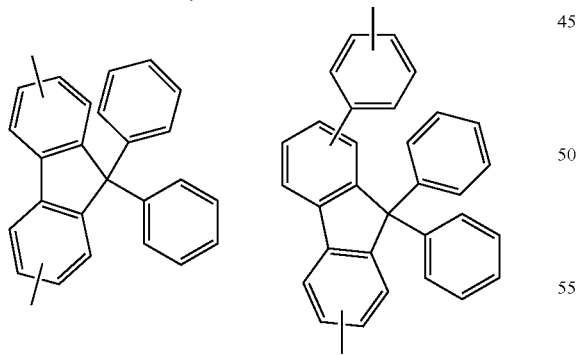

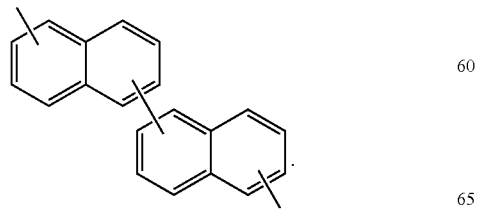

4. The compound of claim 1, where the compound represented by Formula 2 is represented by any one of the following Formulas:

[Formula 1-1]

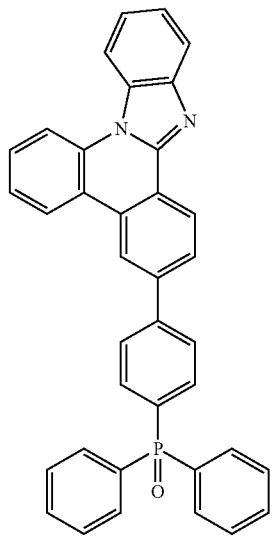

[Formula 1-2]

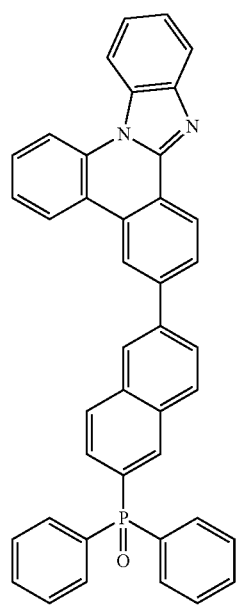

[Formula 1-3]
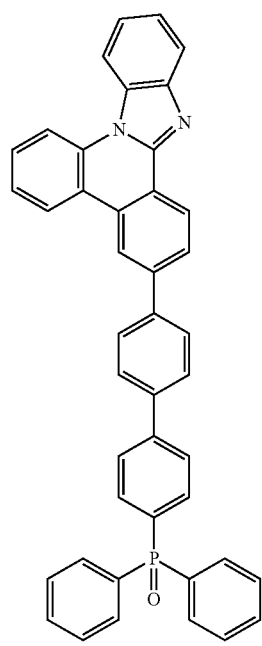
[Formula 1-4]
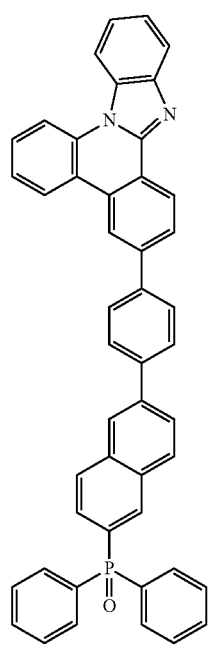
[Formula 1-5]
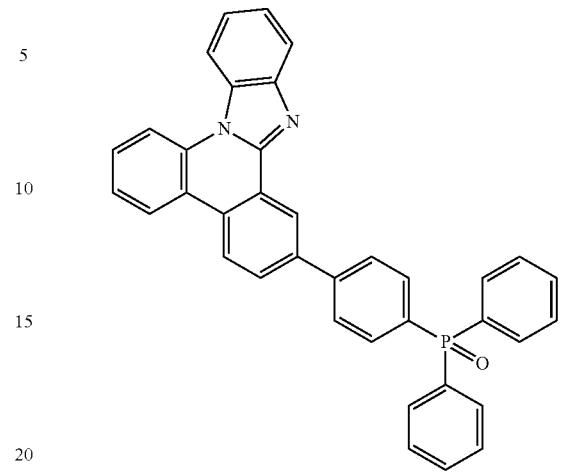
[Formula 1-6]
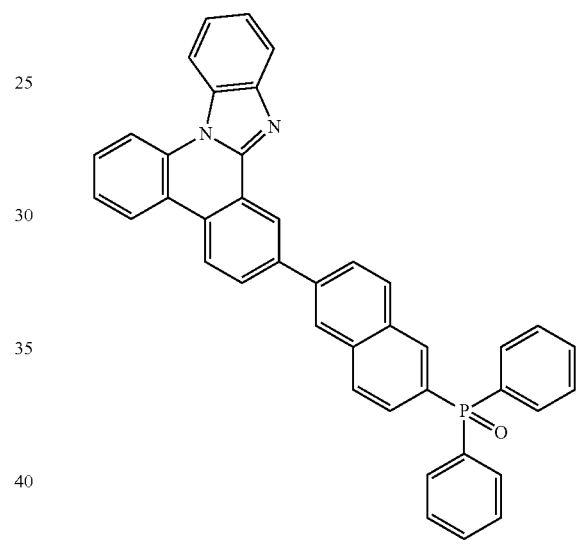
[Formula 1-7]
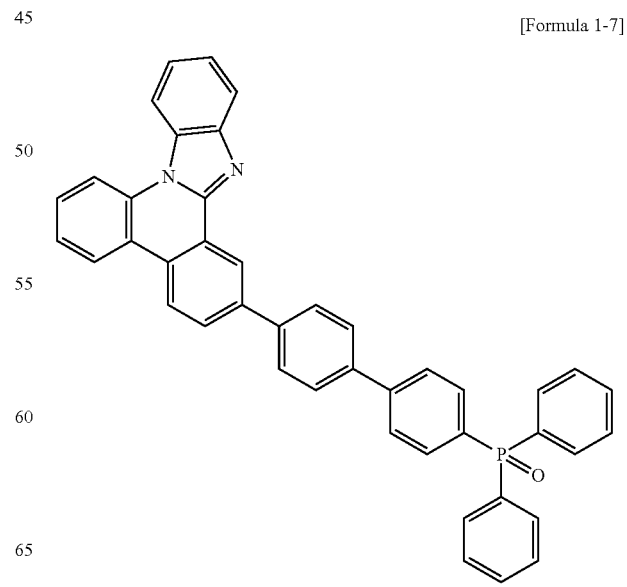

[Formula 1-8]
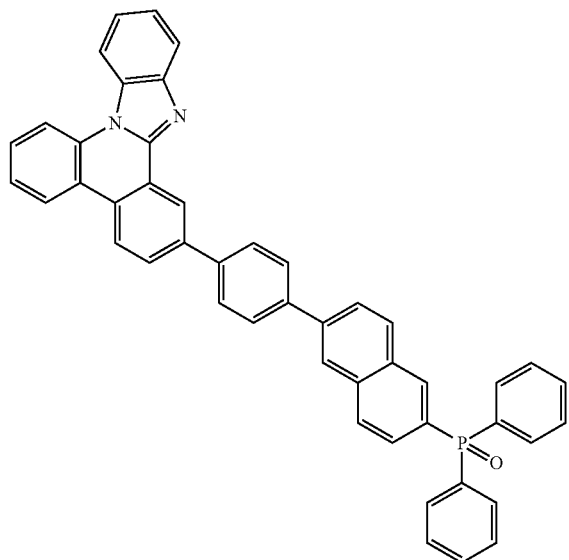
[Formula 1-9]
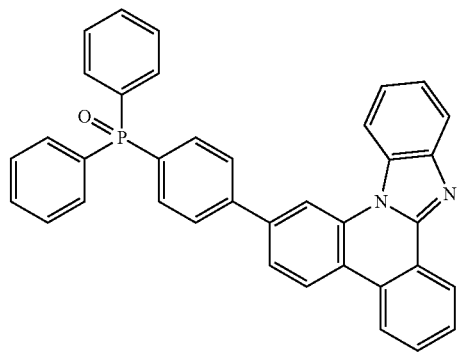
[Formula 1-10]
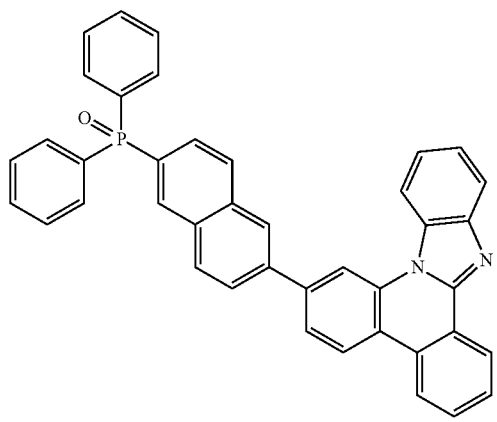
[Formula 1-11]
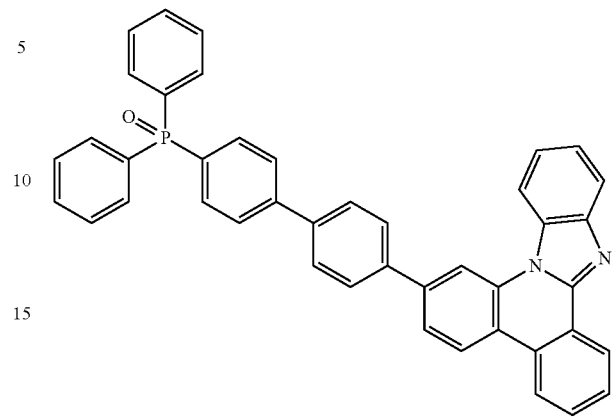
[Formula 1-12]
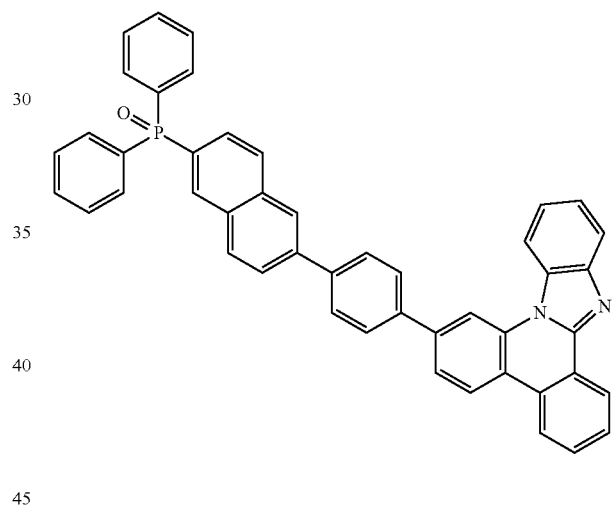
[Formula 1-13]
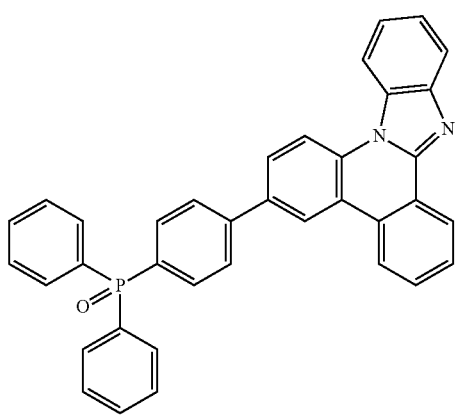

[Formula 1-14]
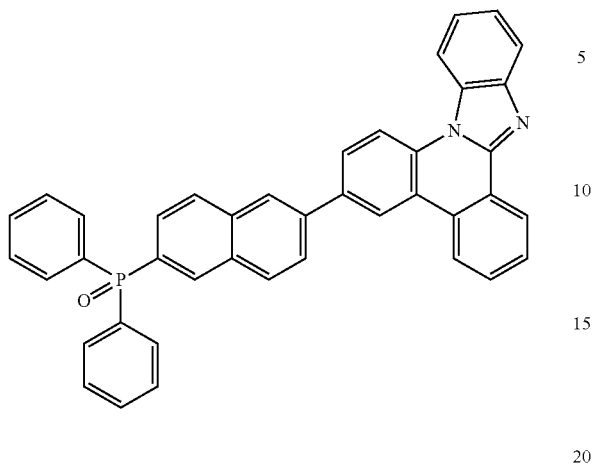
[Formula 1-15]
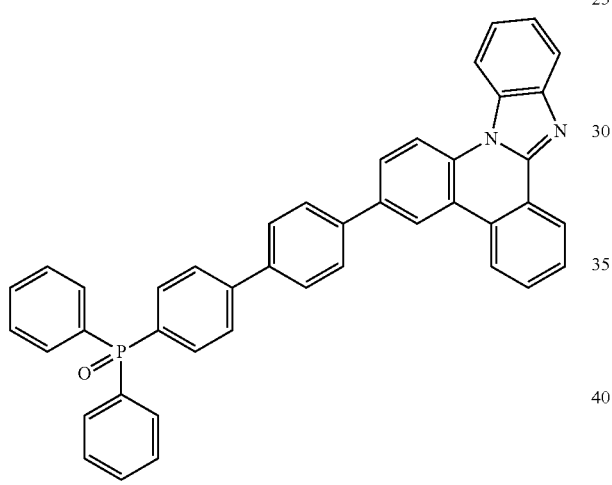
[Formula 1-16]
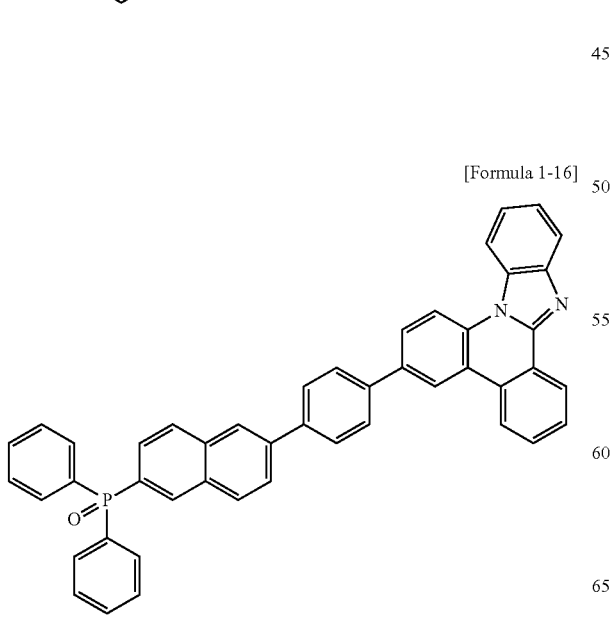
[Formula 1-17]
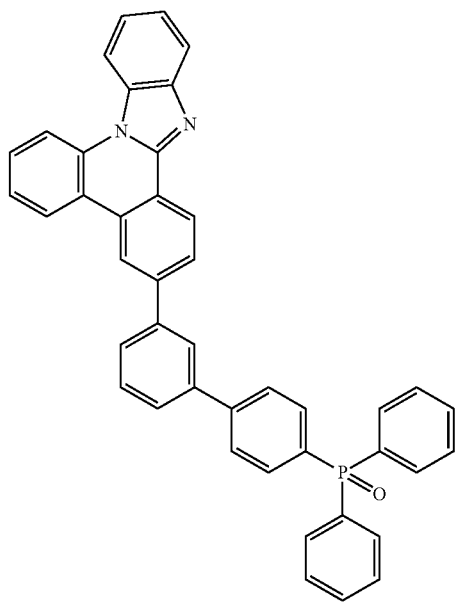
[Formula 1-18]

[Formula 1-19]
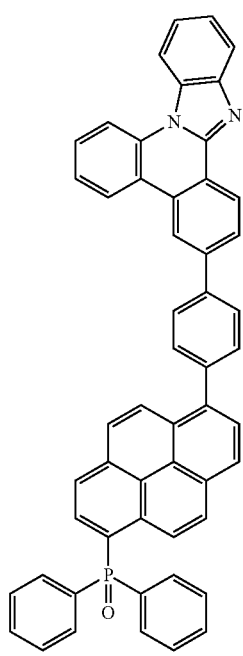
[Formula 1-20]
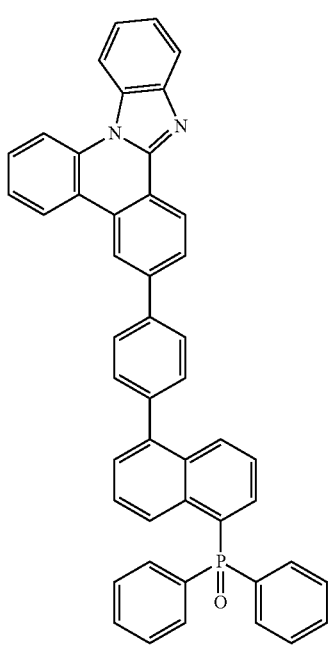
[Formula 1-21]
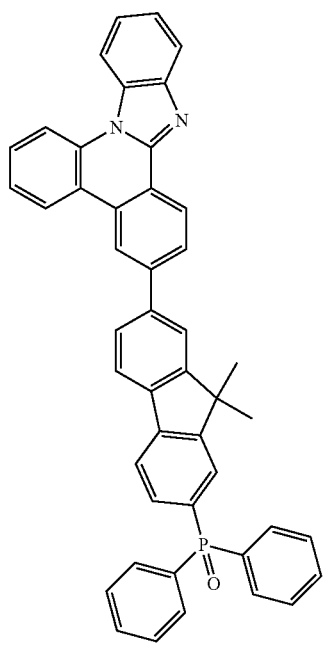
[Formula 1-22]
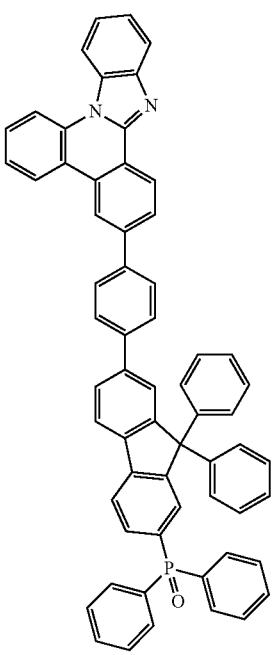

[Formula 1-23]
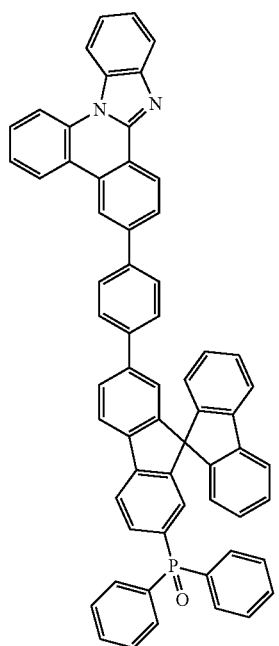
[Formula 1-25]
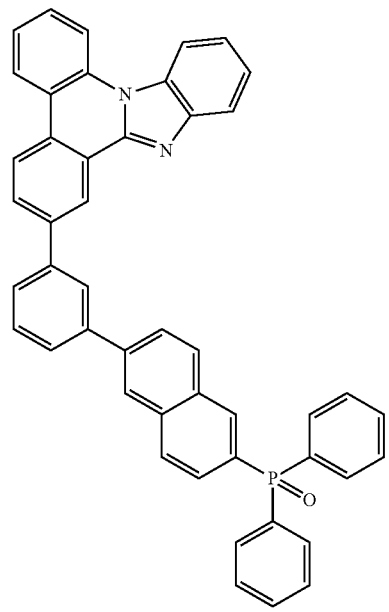
[Formula 1-24]
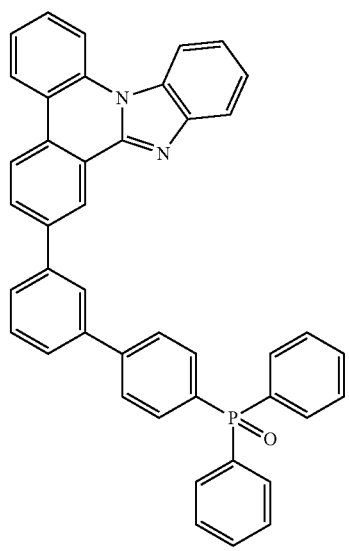
[Formula 1-26]
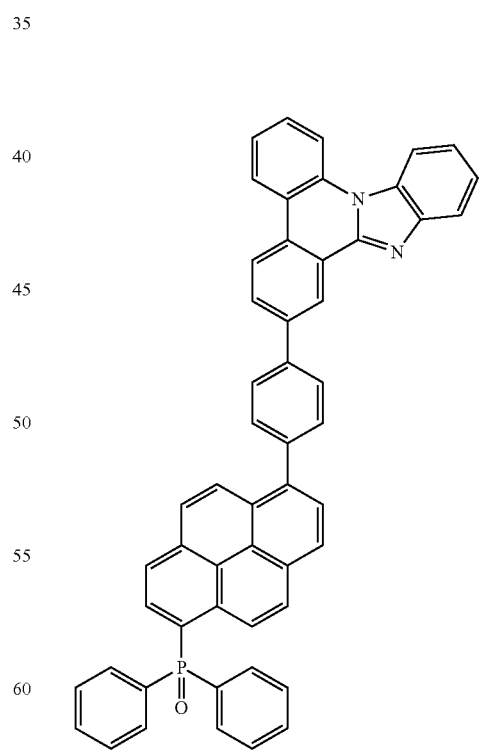

[Formula 1-27]
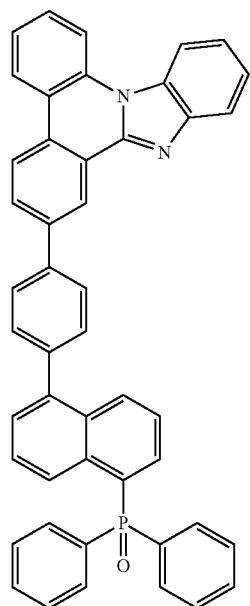
[Formula 1-28]
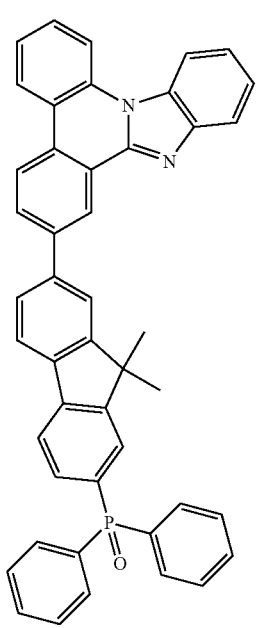
[Formula 1-29]
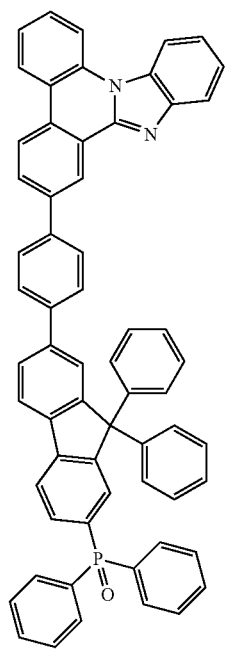
[Formula 1-30]
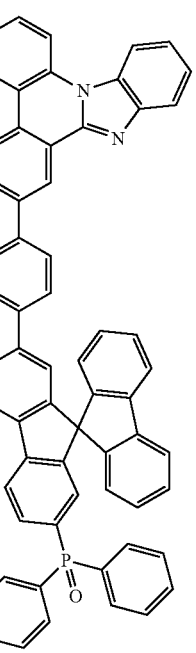

[Formula 1-31]
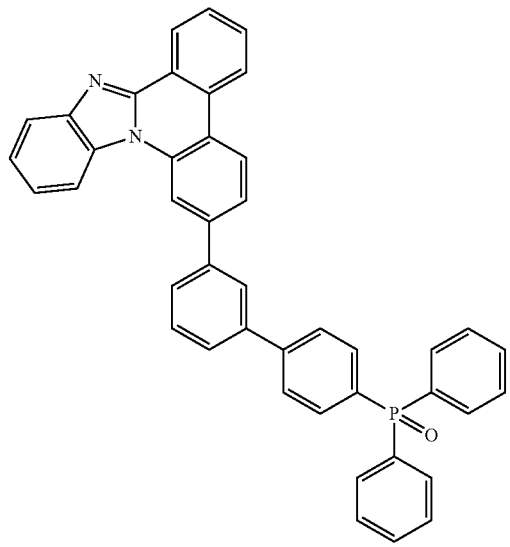
[Formula 1-33]
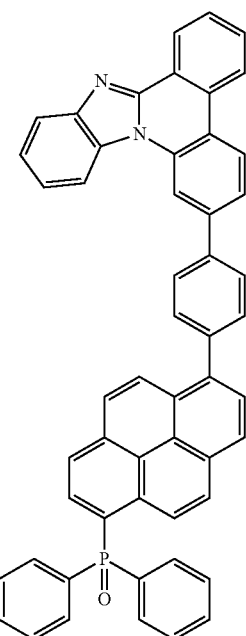
[Formula 1-32]
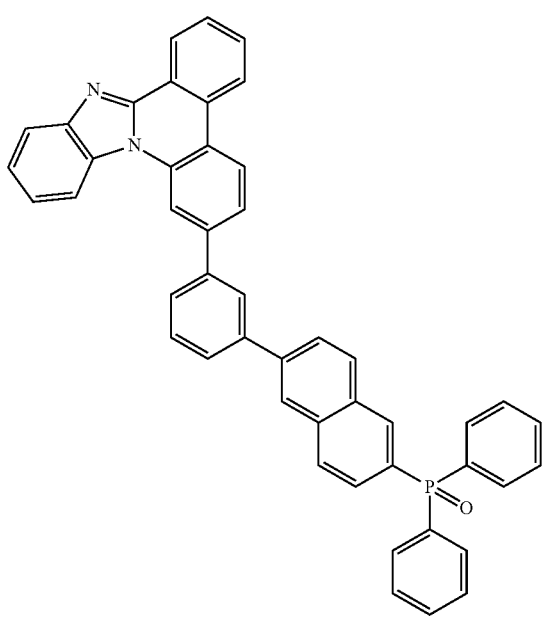
[Formula 1-34]
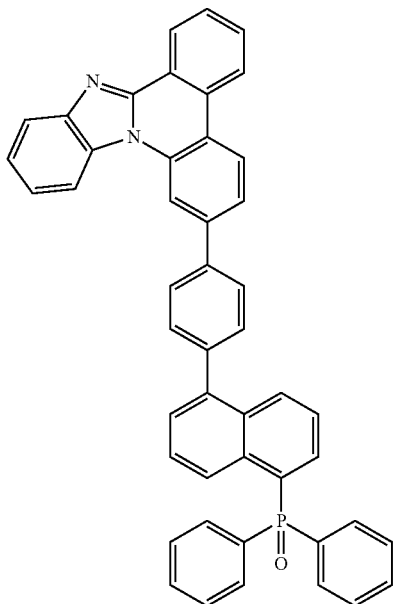

[Formula 1-35]
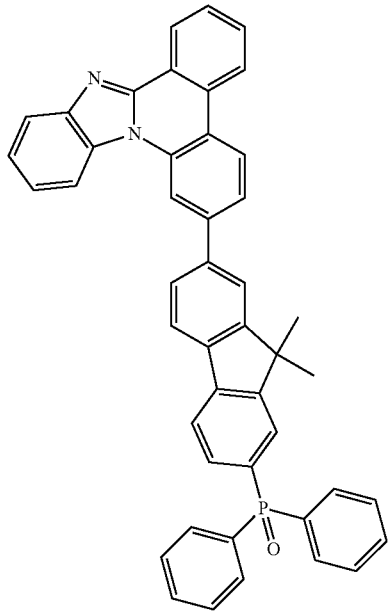
[Formula 1-36]
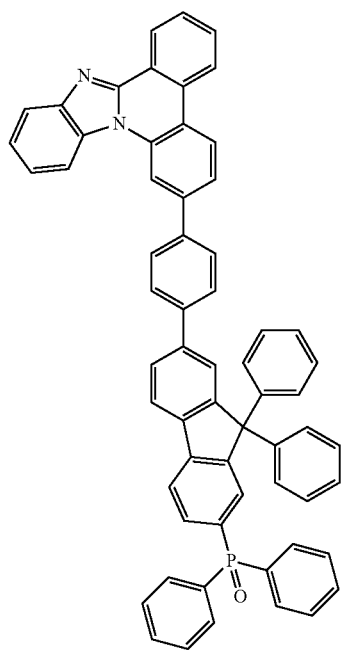
[Formula 1-37]
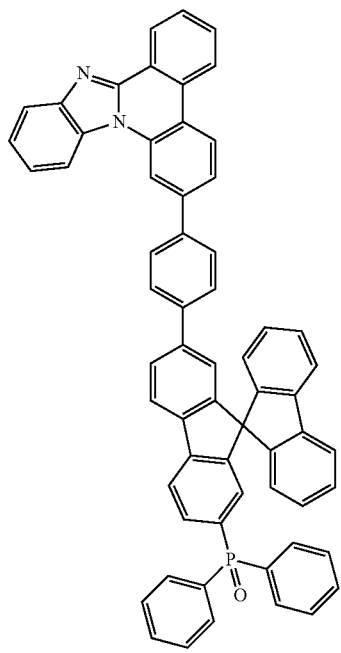
[Formula 1-38]
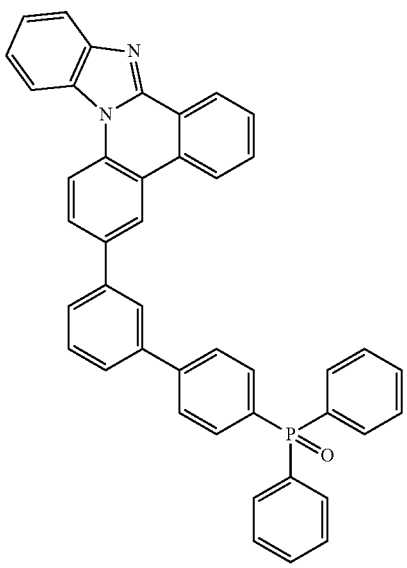

[Formula 1-39]
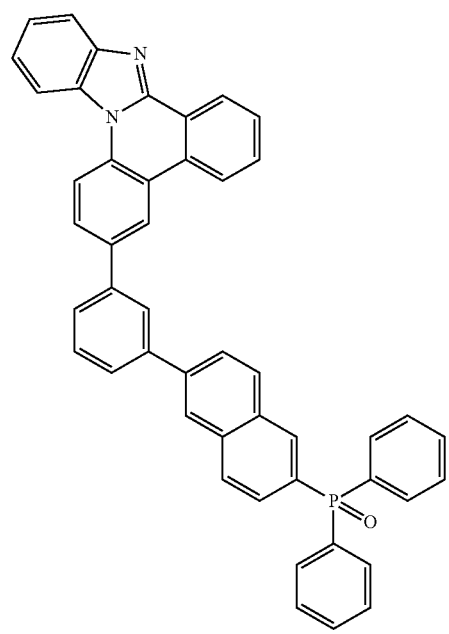
[Formula 1-40]
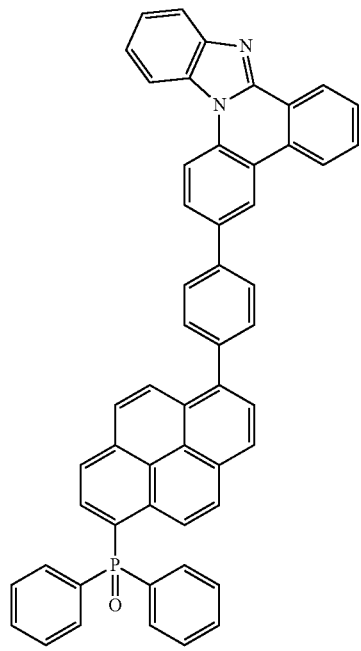
[Formula 1-41]
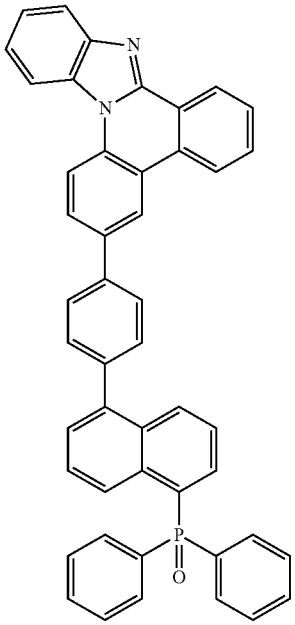
[Formula 1-42]
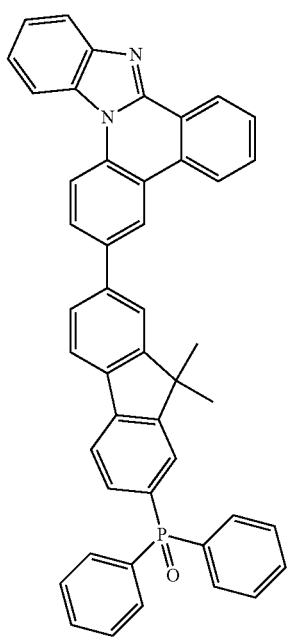

[Formula 1-43]
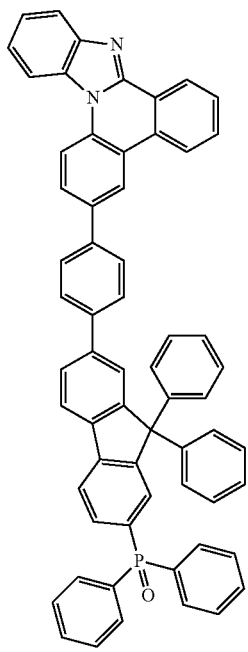
[Formula 1-45]
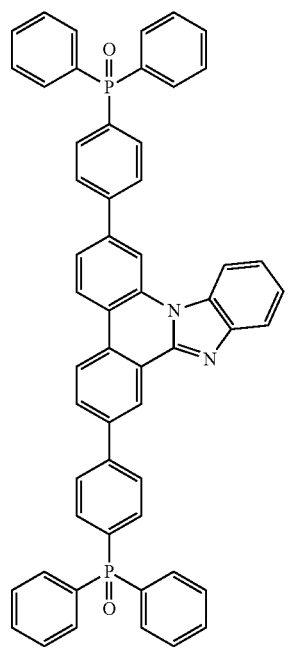
[Formula 1-44]
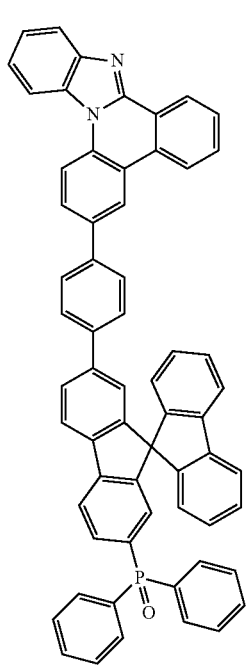
[Formula 1-46]
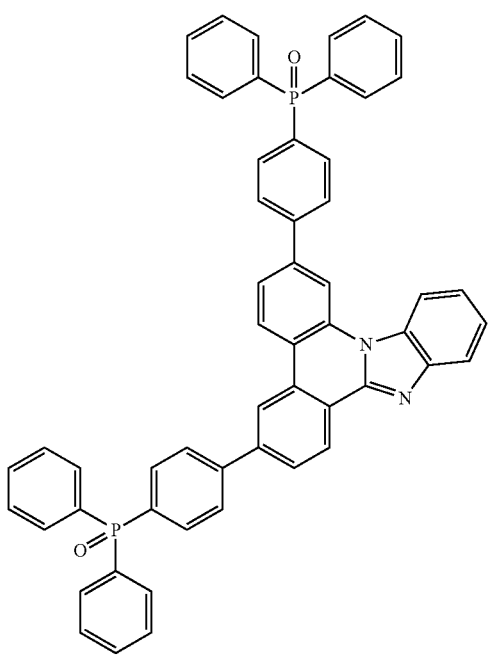

[Formula 1-47]
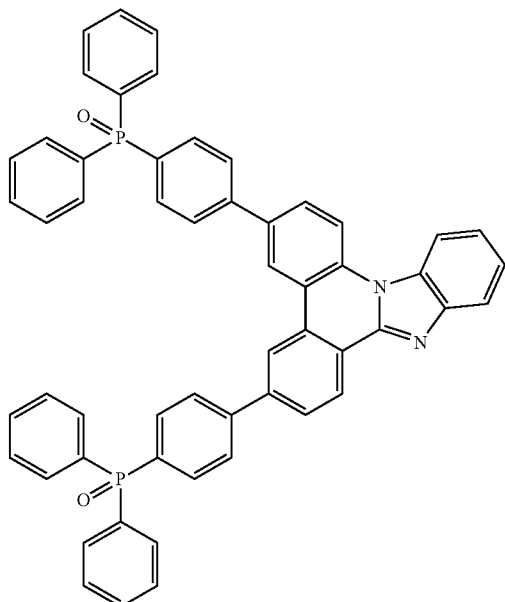
[Formula 1-48]
[Formula 1-49]
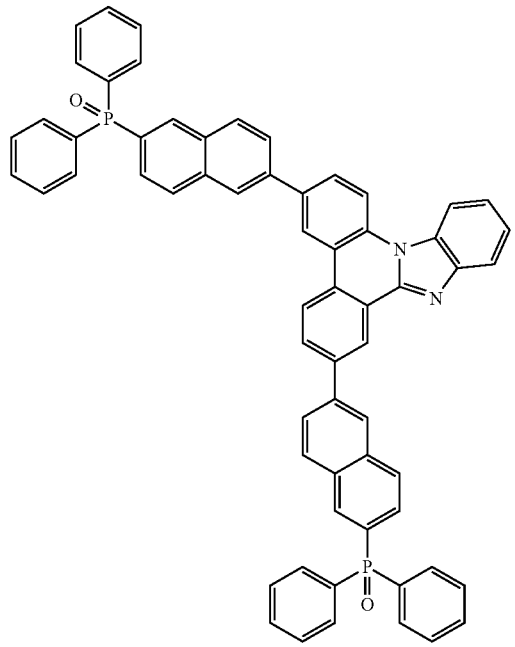
[Formula 1-50]
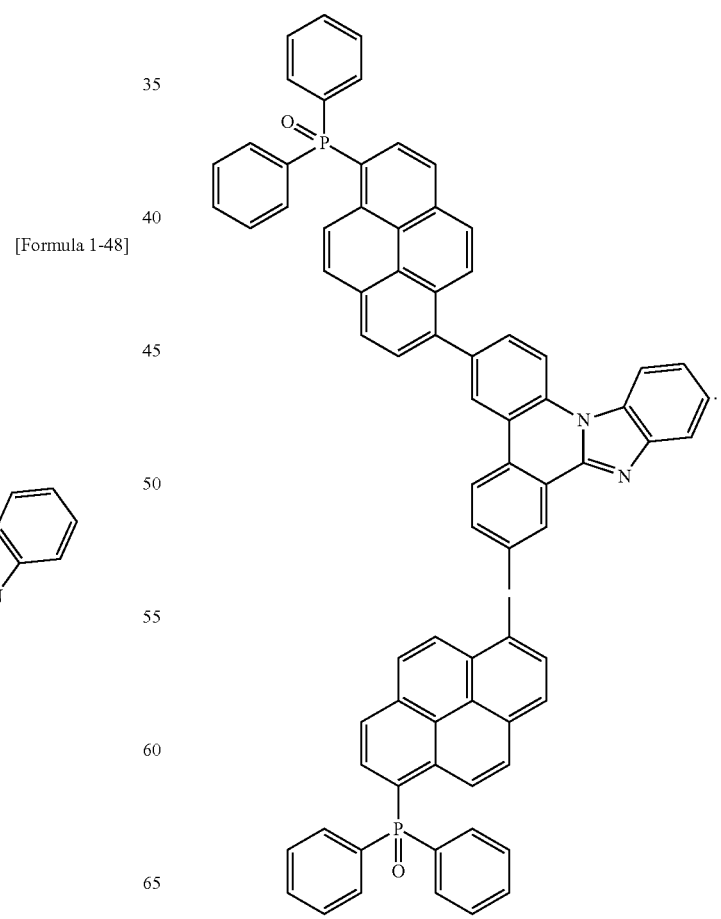

[Formula 1-51]
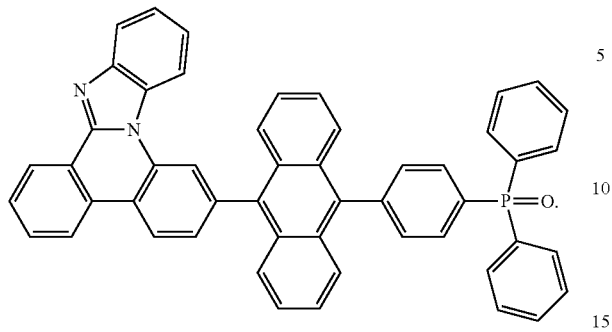
* * * * *